US009146663B2

(12) United States Patent
Kreeger et al.

(10) Patent No.: US 9,146,663 B2
(45) Date of Patent: Sep. 29, 2015

(54) DISPLAYING COMPUTER-AIDED DETECTION INFORMATION WITH ASSOCIATED BREAST TOMOSYNTHESIS IMAGE INFORMATION

(71) Applicant: HOLOGIC, INC., Marlborough, MA (US)

(72) Inventors: Kevin A. Kreeger, Sunnyvale, CA (US); Julian Marshall, Los Altos, CA (US); Georgia K. Hitzke, Boston, MA (US); Haili Chui, Fremont, CA (US)

(73) Assignee: Hologic, Inc., Marlborough, MA (US)

( * ) Notice: Subject to any disclaimer, the term of this patent is extended or adjusted under 35 U.S.C. 154(b) by 183 days.

(21) Appl. No.: 14/037,821

(22) Filed: Sep. 26, 2013

(65) Prior Publication Data
US 2014/0033126 A1    Jan. 30, 2014

Related U.S. Application Data

(63) Continuation-in-part of application No. 12/899,523, filed on Oct. 6, 2010, now Pat. No. 8,547,402.

(60) Provisional application No. 61/249,311, filed on Oct. 7, 2009.

(51) Int. Cl.
*G06F 3/0484* (2013.01)
*G06F 19/00* (2011.01)
(Continued)

(52) U.S. Cl.
CPC .......... *G06F 3/04847* (2013.01); *G06F 19/321* (2013.01); *G06F 19/3406* (2013.01);
(Continued)

(58) Field of Classification Search
CPC ......... G06T 19/00; G06T 17/20; G06T 17/00; G06T 15/10; G06T 15/00; G09G 5/14; G09G 2340/125; G09G 5/395; G09G 2340/10; G06F 3/14
See application file for complete search history.

(56) References Cited

U.S. PATENT DOCUMENTS

| 5,729,620 A | 3/1998 | Wang |
| 5,815,591 A | 9/1998 | Roehrig et al. |

(Continued)

FOREIGN PATENT DOCUMENTS

| WO | WO 00/52641 | 9/2000 |
| WO | WO 02/056240 | 7/2002 |

(Continued)

OTHER PUBLICATIONS

PCT International Search Report and Written Opinion for PCT/US2010/051708, applicant Hologic, Inc., forms PCT/ISA/210, 220 and 237, dated Jun. 17, 2011, 27 pages.

(Continued)

*Primary Examiner* — Todd Buttram
(74) *Attorney, Agent, or Firm* — Vista IP Law Group, LLP

(57) ABSTRACT

Methods, systems, and related computer program products for processing and displaying computer-aided detection (CAD) information associated with medical breast x-ray images, such as breast x-ray tomosynthesis volumes, are described. An interactive graphical user interface for displaying a tomosynthesis data volume is described that includes a display of a two-dimensional composited image having slabbed sub-images spatially localized to marked CAD findings. Also described is a graphical navigation tool for optimized CAD-assisted viewing of the data volume, comprising a plurality of CAD indicator icons running near and along a slice ruler, each CAD indicator icon spanning a contiguous segment of the slice ruler and corresponding in depthwise position and extent to a subset of image slices spanned by the associated CAD finding, each CAD indicator icon including at least one single-slice highlighting mark indicating a respective image slice containing viewable image information corresponding to the associated CAD finding.

18 Claims, 14 Drawing Sheets

(51) Int. Cl.
    *G06T 19/00*     (2011.01)
    *A61B 6/00*     (2006.01)
    *A61B 6/02*     (2006.01)
    *A61B 6/04*     (2006.01)

(52) U.S. Cl.
    CPC ............ *G06F19/3437* (2013.01); *G06T 19/00* (2013.01); *A61B 6/025* (2013.01); *A61B 6/0414* (2013.01); *A61B 6/466* (2013.01); *A61B 6/467* (2013.01); *A61B 6/5217* (2013.01); *A61B 6/5294* (2013.01); *G06T 2200/24* (2013.01); *G06T 2210/41* (2013.01); *G06T 2219/004* (2013.01)

(56) References Cited

U.S. PATENT DOCUMENTS

| | | |
|---|---|---|
| 6,014,452 A | 1/2000 | Zhang et al. |
| 6,075,879 A | 6/2000 | Roehrig et al. |
| 6,301,378 B1 | 10/2001 | Karssemeijer et al. |
| 6,574,357 B2 | 6/2003 | Wang |
| 6,748,044 B2 | 6/2004 | Sabol et al. |
| 6,909,795 B2 | 6/2005 | Tecotzky et al. |
| 7,218,766 B2 | 5/2007 | Eberhard et al. |
| 7,298,877 B1 | 11/2007 | Collins et al. |
| 7,630,533 B2 | 12/2009 | Ruth et al. |
| 2007/0047793 A1 | 3/2007 | Wu et al. |
| 2007/0177780 A1 | 8/2007 | Chui |
| 2008/0152086 A1 | 6/2008 | Hall et al. |
| 2008/0155451 A1 | 6/2008 | Lundstrom et al. |
| 2008/0155468 A1 | 6/2008 | Rosander et al. |
| 2009/0034684 A1 | 2/2009 | Bernard et al. |
| 2009/0080765 A1 | 3/2009 | Bernard et al. |
| 2009/0087067 A1 | 4/2009 | Khorasani |
| 2009/0312640 A1* | 12/2009 | Wang et al. .................. 600/443 |
| 2010/0141654 A1 | 6/2010 | Neemuchwala et al. |
| 2013/0028374 A1* | 1/2013 | Gkanatsios et al. ............ 378/37 |

FOREIGN PATENT DOCUMENTS

| | | |
|---|---|---|
| WO | WO 2008/020062 | 2/2008 |
| WO | WO 2009/038948 | 3/2009 |

OTHER PUBLICATIONS

Alonzo-Proulx, et. al., "Validation of a Method for Measuring the Volumetric Breast Density From Digital Mammograms," Phys Med Biol 55(11):3027-44 (2010).

Ed H. Chi "A Taxanomy of visualization techniques using the data state reference model", Xerox Palo Alto Research Center, Information Visualization, 2000. INFOVIS 2000. IEEE Symposium on Salt Lake City UT, USA Oct. 9-10, 2000, Los Alamitos, CA, USA, IEEE Comput. Soc, US, Oct. 9, 2000, pp. 69-75, (7 pages).

Pace D. et al: "MR-guided Prostate Interventions with 3D Slicer and the NA-MIC Kit", National Alliance for Medical Image Computing, NCIGT-SNR Tutorial, Jan. 31, 2009, p. Slide 23 (1 page).

Brijesh Verma, Peter McLeod, Alan Klevansky, "A novel soft cluster neural network for the classifications of suspicious areas in digital mammograms", Pattern Recognition, Elsevier, GB, vol. 42, No. 9, Sep. 1, 2009, pp. 1845-1852, (8 pages).

"Digital Imaging and Communications in Medicine Part 16: Content Mapping Resource," National Electrical Manufacturers Association, PS 3.16-2009 (968 pages).

* cited by examiner

DISPLAYING COMPUTER-AIDED DETECTION INFORMATION WITH ASSOCIATED BREAST TOMOSYNTHESIS IMAGE INFORMATION

CROSS-REFERENCE TO RELATED APPLICATIONS

This application is a continuation of U.S. patent application Ser. No. 12/899,253, filed Oct. 6, 2010, now U.S. Pat. No. 8,547,402, which claims the benefit of U.S. Provisional Patent Application Ser. No. 61/249,311, filed Oct. 7, 2009, entitled "Device and Method for Displaying CAD Marks in Three Dimensional Images," which is incorporated by reference herein. The subject matter of one or more preferred embodiments described herein relates to the subject matter of the commonly assigned U.S. Ser. No. 12/330,176, filed Dec. 8, 2008, entitled "Device and Method for Displaying Feature Marks Related to Features in Three Dimensional Images on Review Stations," which published on Jun. 10, 2010 as US 2010/0141654A1 and which is incorporated by reference herein.

FIELD

This patent specification relates to the computer-aided detection (CAD) of anatomical abnormalities in medical images. More particularly, this patent specification relates to the display of CAD results for two-dimensional and three-dimensional image volumes, with one or more preferred embodiments having particularly advantageous application to two-dimensional projection x-ray mammograms of the breast and/or x-ray tomosynthesis image volumes of the breast.

BACKGROUND

Progress toward all-digital medical imaging environments has substantially increased the speed at which large amounts of medical image information can be accessed and displayed to a radiologist. X-ray based imaging for breast cancer screening/diagnosis is a particularly important field that is experiencing such information-expanding technological progress. Historically, breast cancer screening/diagnosis has been based on conventional x-ray projection mammography techniques in which an x-ray source projects x-rays through a breast that is immobilized by compression against a breast platform. A two-dimensional projection image of the breast, referred to as a mammogram, is captured by a film or digital x-ray detector located beneath the breast platform.

Although conventional x-ray mammography is currently recognized as one of the best FDA-approved methods for detecting early forms of breast cancer, it is still possible for cancers to be missed during radiological viewing of the mammogram. A variety of factors, such as breast density, may contribute to the failure to detect breast cancers.

For these and other reasons, substantial attention and technological development has been dedicated toward breast x-ray tomosynthesis, which is similar in many respects to conventional x-ray mammography except that the x-ray source is no longer stationary, but instead rotates through a limited angle relative to the breast platform normal (e.g., −15 degrees to +15 degrees) while several projection images (e.g., 10-15 projection images) are acquired by the x-ray detector. The several projection images are then mathematically processed to yield a number (e.g., 40-60) of tomosynthesis reconstructed images, each corresponding to a different slice of breast tissue, which can then be examined by the radiologist. Whereas a particular cancerous lesion positioned within a region of dense fibroglandular tissue might have been obscured in a single conventional x-ray mammogram view, that lesion could be readily apparent within a set of tomosynthesis reconstructed images representative of individual slices through the dense fibroglandular tissue.

Although x-ray tomosynthesis imaging and computed tomography (CT) imaging are both generally considered to be three dimensional imaging modalities, there are differences between these two modalities that can have an impact on the way their associated data volumes are best processed and/or reviewed for the detection of anatomical abnormalities. Concordant with the favorability of x-ray tomosynthesis imaging over CT imaging from the perspectives of radiation dose and cost/complexity of the image acquisition equipment, the number and angular range of projection images for x-ray tomosynthesis imaging is less than for CT imaging, which requires a minimum angular span of at least 180 degrees plus a fan beam angle. However, unlike with CT imaging, x-ray tomosynthesis imaging is not capable of providing a "true" value for the x-ray absorption property of any particular point in the imaged volume, but instead only provides such value in inseparable combination with varyingly "blurred" versions of the absorption property from other parts of the imaged volume. The number of distinct reconstructed image slices containing useful and anatomically differentiating information is substantially less for x-ray tomosynthesis than for CT imaging, and x-ray tomosynthesis reconstructed images are often artifact-laden and highly anisotropic according to the particular range and orientation of the tomosynthesis imaging arc traversed. For these reasons, x-ray tomosynthesis imaging is sometimes termed a "quasi" three-dimensional imaging modality, with CT imaging representing a "true" three-dimensional imaging modality. While the preferred embodiments infra are particularly advantageous when applied to the peculiarities of x-ray tomosynthesis image volumes, it is nevertheless to be appreciated that one or more aspects of the described embodiments can be extended to the processing and display of CT data volumes without departing from the scope of the present teachings.

Computer-aided detection (CAD) refers to the use of computers to analyze medical images to detect anatomical abnormalities therein, and/or the use of computers to otherwise process image information in a manner that facilitates perception of the medical image information by a radiologist. Sometimes used interchangeably with the term computer-aided detection are the terms computer-aided diagnosis, computer-assisted diagnosis, or computer-assisted detection. CAD findings are most often communicated in the form of annotation maps comprising graphical annotations (CAD markers) overlaid on a diagnostic-quality or reduced-resolution version of the medical image. Substantial effort and attention has been directed to increasing the analysis capabilities of CAD systems, resulting in ever-increasing amounts of information that is available to the radiologist for review. Thousands of CAD systems for conventional x-ray mammography are now installed worldwide, and are used to assist radiologists in the interpretation of millions of mammograms per year.

Development and commercialization of CAD systems capable of identifying anatomical abnormalities in x-ray tomosynthesis data volumes also continues. However, in progressing from conventional x-ray mammography to breast x-ray tomosynthesis imaging, practical issues arise with regard to the rising volume of data requiring review by the radiologist. Whereas there are usually just four conventional x-ray mammogram images per patient, there can be hundreds of tomosynthesis reconstructed image slices (e.g., 40-60 slices for each of the four views). As more visual information becomes available, an important challenge is to present such information to the radiologist effectively and efficiently such that screening for abnormalities can be done thoroughly and effectively, and yet in a reasonable time to be practical, and diagnostic assessment can also be facilitated.

Of particular importance is the manner in which an image review workstation displays CAD markers to the radiologist in the large stack of tomosynthesis reconstructed images. For CAD markers displayed during a first reading, it is desirable that the CAD markers not be overly obtrusive on their corresponding image, it is also desirable that they not be readily overlooked as the radiologist moves through his/her examination of the image slices. For CAD markers displayed as part of a second reading, the CAD marks may be more obviously displayed, but due to the sheer volume of available tomosynthesis image slices, it is still possible that CAD markers may be overlooked. One problem that may be encountered when reviewing CAD markers in a tomosynthesis data set is that the markers are not located on all of the image slices. In fact, in a given set it may be that CAD markers are only located on a few of the images. One method of facilitating a more efficient CAD review during a radiological reading is described in the commonly assigned U.S. Pat. No. 7,630,533B2, which is incorporated by reference herein, and which describes a ruler identifying the slices for display. Each slice that contains a marker has an indicator positioned next to the ruler. With such an arrangement a reviewer can quickly identify a slice with a CAD mark and transition rapidly to the slice of interest by selecting the marker that is near the ruler, thereby increasing reviewing efficiency.

Another method of increasing the efficiency of CAD review during radiological reading is described in the commonly assigned US 2009/0087067A1, which is incorporated by reference herein, and which describes including CAD proximity markers on one or more image slices neighboring those that contain actual CAD markers, such that a reviewer who is quickly paging through many slices will be less likely to miss the CAD-marked slices. Both of the above techniques reduce the chance that an image slice will be overlooked during review, yet each still require sifting through multiple images to identify those images with the most relevant information. Other issues arise as would be readily apparent to one skilled in the art in view of the present disclosure.

SUMMARY

Provided according to one or more preferred embodiments are methods, systems, and related computer program products for processing and displaying computer-aided detection (CAD) information in conjunction with breast x-ray tomosynthesis data volumes and/or breast x-ray projection images. In one preferred embodiment, an interactive user interface for displaying breast x-ray tomosynthesis information and related CAD information is provided. In operation, a two-dimensional breast x-ray tomosynthesis reconstructed image slices corresponding to a respective plurality of slice depths in a breast volume is received, along with a plurality of CAD findings associated with the breast volume. Each CAD finding identifies a subset of the image slices spanned by a suspected anatomical abnormality, as well as locations therein of the suspected anatomical abnormality. The received image slices and the received CAD findings are processed to generate a two-dimensional composited image of the breast volume, wherein the two-dimensional composited image comprises (a) a first slabbed sub-image of a first localized neighborhood that laterally encompasses a first of the CAD findings, the first slabbed sub-image being formed by slabbing the subset of image slices spanned by the first CAD finding, and (b) a non-CAD-specific sub-image of at least one neighborhood of the breast not associated with any of the CAD findings. The two-dimensional composited image is then displayed on a user display. Preferably, the first slabbed sub-image does not include contributions from image slices not spanned by the first CAD finding, and the non-CAD-specific sub-image is derived from image information other than the particular subset of image slices slabbed to form the slabbed sub-image.

According to another preferred embodiment, an interactive user interface for displaying breast x-ray tomosynthesis information and related CAD information is provided, in which there is received the above-described image slices and CAD findings. Displayed on a user display is a two dimensional diagnostic image comprising either (i) a single one of the received image slices, or (ii) a plurality of depthwise adjacent ones of said received image slices slabbed together, the diagnostic image thus being characterized by an image depth and an image thickness. Provided on the user display in visual proximity to the two dimensional diagnostic image is a graphical depth navigation tool configured to graphically communicate to a user the image depth and the image thickness of the currently displayed diagnostic image, and to allow user control thereof. The graphical depth navigation tool comprises (a) a slice ruler spatially extending in a first direction representative of said image depth, and (b) a slice slider icon disposed along the slice ruler at a user-controllable position corresponding to the image depth. Further displayed on the user display is a plurality of CAD indicator icons corresponding respectively to the plurality of CAD findings, each CAD indicator icon running near and along the slice ruler and spanning a contiguous segment thereof that corresponds in depthwise position and extent to the subset of image slices spanned by the associated CAD finding. Further displayed is at least one single-slice highlighting mark on each of the CAD indicator icons, each single-slice highlighting mark being positioned on its associated CAD indicator icon at a location indicative of the slice depth of a respective one of the subset of image slices spanned by the associated CAD finding and containing viewable image information corresponding to that associated CAD finding.

According to another preferred embodiment, an interactive user interface for displaying breast x-ray tomosynthesis information and related CAD information is provided, in which there is received the above-described image slices and CAD findings, and in which there is displayed the above-described two-dimensional diagnostic image associated with the breast volume. Each of the image slices corresponds to a slice in the breast volume that is generally transverse to a direction of compression. Further displayed on the user display in visual proximity to the two dimensional diagnostic image is a graphical navigation tool configured to graphically communicate to a user the image depth and image thickness of the currently displayed diagnostic image, and to allow user control thereof. The graphical navigation tool comprises a two-dimensional outline image in miniaturized form of the breast volume as projected onto a plane along the direction of compression, the two-dimensional outline image having a depth dimension corresponding to the direction of compression and a lateral dimension normal to said depth dimension. The graphical navigation tool further comprises a slice slider bar extending across at least a portion of the outline image in a direction parallel to the lateral dimension, the slice slider bar having a user-controllable position in the depth dimension that corresponds to the image depth of the currently displayed diagnostic image. Further displayed on the user display is a plurality of CAD indicator icons corresponding respectively to the plurality of CAD findings, each CAD indicator icon being positioned on the outline image at a location representative of the location of the associated CAD finding in the breast volume. Each CAD indicator icon has a position and extent in the depth dimension that corresponds to the slice depths of the image slices spanned by the associated CAD finding.

Provided according to another preferred embodiment is a method for processing and displaying information related to a plurality of breast x-ray tomosynthesis cases, each case comprising at least one breast x-ray tomosynthesis data volume associated with at least one breast of a patient. For each case, a target count "N" representing a target number of marked CAD findings to be displayed to a user on a review workstation in conjunction with the at least one data volume is determined. Importantly, the target count N is independent of any breast tissue image information contained in any of the data volumes for any of the cases. For each case, a set of candidate CAD findings is received, each candidate CAD finding being associated with a potentially suspicious lesion in the at least one breast as identified by a CAD algorithm and characterizing the potentially suspicious lesion by a plurality of computed features including a certainty of finding metric. For each case, up to the target count N of the candidate CAD findings are designated as being marked CAD findings according to the steps of (a) designating all of the candidate CAD findings as marked CAD findings if the number of candidate CAD findings in the received set is less than or equal to the target count N, and (b) if the number of candidate CAD findings is greater than the target count N, processing the candidate CAD findings according to their computed features to designate exactly N of them as marked CAD findings. For each of the cases, the at least one data volume is displayed to the user on the review workstation with viewable annotation markers thereon corresponding to each of the marked CAD findings, the review workstation not displaying annotation markers corresponding to the candidate CAD findings that are not marked CAD findings. The user experience is thereby weighted more toward consistency in the number of marked CAD findings per case and less toward uniform evaluation of the candidate CAD findings across different cases.

Provided according to another preferred embodiment is a method for processing and displaying information related to a plurality of breast x-ray tomosynthesis data volumes, the method being analogous to the above-described method except that there is specified a target count "N" representing a target number of marked CAD findings to be displayed per data volume, regardless of the case membership of that data volume. For each data volume, up to the target count N of the candidate CAD findings are designated as being marked CAD findings according to the steps of (a) designating all of the candidate CAD findings as marked CAD findings if the number of candidate CAD findings in the received set is less than or equal to the target count N, and (b) if the number of candidate CAD findings is greater than the target count N, processing the candidate CAD findings according to their computed features to designate exactly N of them as marked CAD findings. The user experience is thereby weighted more toward consistency in the number of marked CAD findings per data volume and less toward uniform evaluation of the candidate CAD findings across different data volumes.

Provided according to another preferred embodiment is a method for processing and displaying CAD findings associated with breast x-ray images in a manner that is at least partially dependent on fibroglandular density characteristics of the breast. A medical x-ray image of a breast is received along with a set of candidate CAD findings associated with the medical x-ray image, each candidate CAD finding identifying a location of a potentially suspicious lesion in the breast and characterizing the potentially suspicious lesion by a plurality of computed features including a certainty of finding metric. There is then computed a fibroglandular tissue density map of the breast that is based at least in part on information associated with the medical x-ray image. The fibroglandular tissue density map characterizes each location therein by a fibroglandular tissue density metric representative of an absolute proportion, by volume, of fibroglandular breast tissue in a local neighborhood of that location. Each of the candidate CAD findings is then designated as being either a marked CAD finding or a non-marked CAD finding based on its associated certainty of finding metric and the fibroglandular tissue density metric at the location thereof. Preferably, in order to be designated as marked CAD findings, candidate CAD findings at locations of higher fibroglandular tissue density require higher certainties of finding than is required for candidate CAD findings at locations of lower fibroglandular tissue density. The medical x-ray image is then displayed to a user on a review workstation with viewable annotation markers thereon corresponding to each of the marked CAD findings, the review workstation not displaying annotation markers corresponding to the non-marked CAD findings.

Provided according to another preferred embodiment is another method for processing and displaying CAD findings in a manner that is at least partially dependent on breast fibroglandular density characteristics, the method comprising receiving the medical x-ray image and CAD findings as described above, and computing the fibroglandular tissue density map as described above. The fibroglandular tissue density map is then processed to detect a contiguous region of the breast therein that is characterized by (i) a fibroglandular tissue density metric that is higher than a predetermined statistical threshold, and (ii) a size and shape that is sufficient to substantially obscure an anatomical abnormality among the high fibroglandular density tissue therewithin. All CAD findings located within the detected contiguous region are then designated as unmarked CAD findings, regardless of their computed features. The medical x-ray image is then displayed to a user on a review workstation with viewable annotation markers thereon corresponding to each of the marked CAD findings, the review workstation not displaying annotation markers corresponding to the non-marked CAD findings.

DETAILED DESCRIPTION

Figure 1:
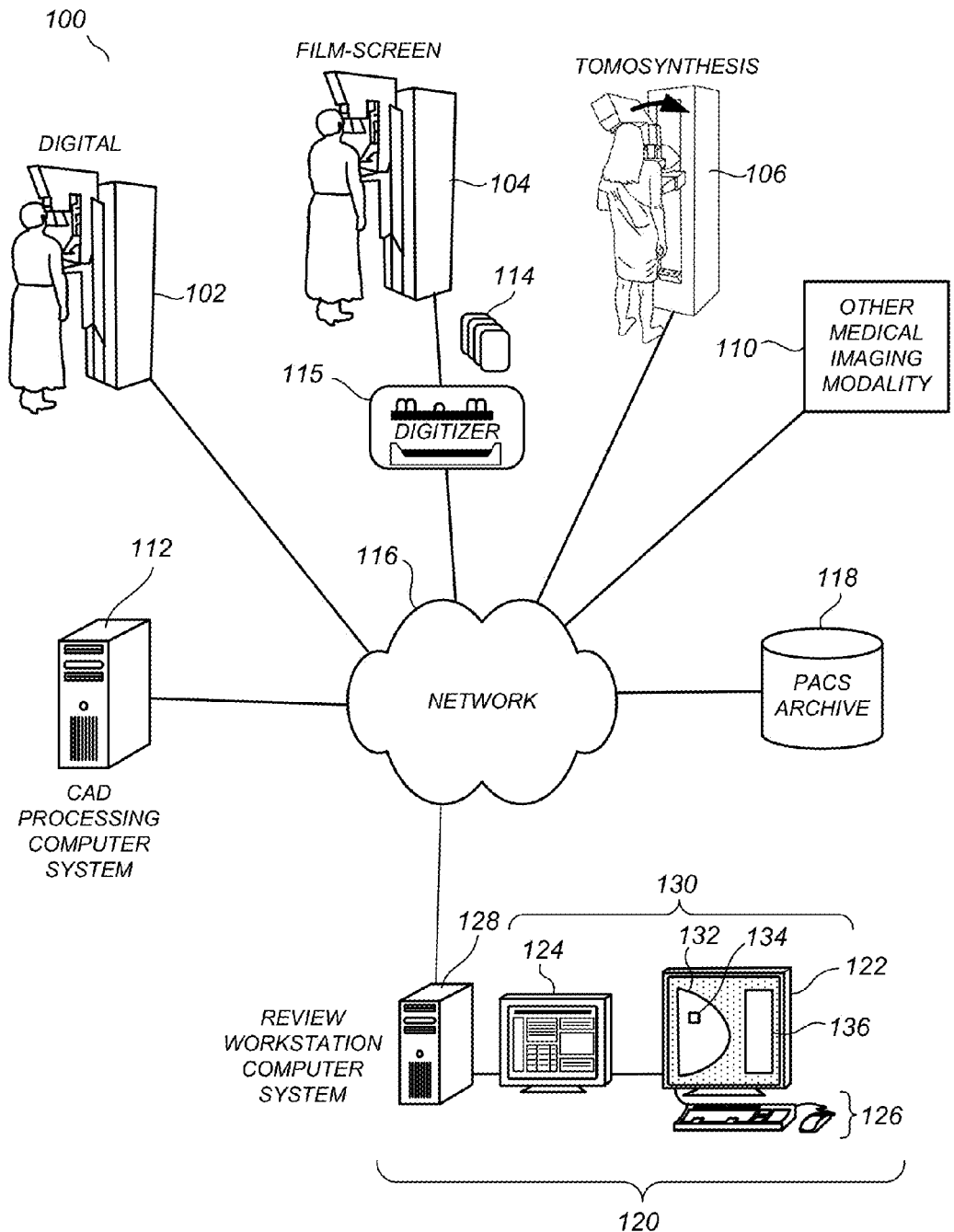
FIG. 1 illustrates a conceptual diagram of a breast x-ray imaging environment including a review workstation for interactive display of breast x-ray information and related computer-aided detection (CAD) information according to a preferred embodiment.

In describing preferred embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Although the following description refers to user interfaces of one or more preferred embodiments to facilitate dynamic review of breast x-ray tomosynthesis data (either during a first or second reading of the image data) it will readily be appreciated by one of skill in the art that one or more concepts of the preferred embodiments may be extended for use in viewing CAD information available in any dimension of a three-dimensional data set provided by any means, and 'displayed' in any manner. Thus the below description should be viewed only as illustrative and not limiting. Although certain terms and definitions will be provided which have particular relevance to breast imaging it will be appreciated that equivalent elements are found in the related arts. For example, although mention may be made to mammograms and tomosynthesis projection images, such images should be viewed as equivalents to any two dimensional image as a part of a three dimensional volume.

That said, the following abbreviations shall have the following definitions throughout this application. The notation Mp refers to a conventional x-ray mammogram, which is a two-dimensional projection image of a breast and encompasses both a digital image as acquired by a flat panel detector or another imaging device and the image after conventional processing to prepare it for display to a health professional or for storage, such as in a PACS system (Picture Archiving and Communication System) of a hospital or another institution. The notation Tp refers to an x-ray tomosynthesis projection image that is similarly two-dimensional but is taken at a respective tomosynthesis projection angle between the breast and the source of the imaging x-rays (typically the focal spot of an X-ray tube), and also encompasses such image as acquired as well as such image after being processed for display or for some other use. The notation Tr refers to a tomosynthesis reconstructed image that is computed from the images Tp according to a tomosynthesis reconstruction algorithm, and represents a slice or slab of the breast as it would appear in a projection x-ray image of that slice at any desired angle, not only at an angle used for Tp or Mp images.

The terms Tp, Tr, and Mp also encompass information, in whatever form, that is sufficient to describe such an image for display, further processing, or storage. The images Mp, Tp and Tr typically are in digital form before being displayed, and are defined by information identifying properties of each pixel in a two-dimensional array of pixels. The pixel values typically relate to respective measured or estimated or computed responses to x-rays of corresponding volumes in the breast (voxels or columns of tissue).

FIG. 1 illustrates a conceptual diagram of a breast x-ray imaging environment 100 including a review workstation 120 for interactive display of breast x-ray information and related computer-aided detection (CAD) information according to one or more of the preferred embodiments. Shown in FIG. 1 is a network 116, which may be a HIS/RIS (Hospital Information System/Radiology Information System) network, to which is coupled a digital mammogram acquisition device 102, a film-screen mammogram acquisition device 104, a tomosynthesis acquisition device 106, and a generalized "other" medical imaging device 110 representative of, for example, magnetic resonance imaging (MRI) acquisition devices and ultrasound acquisition devices.

With reference to FIG. 1, a computer-aided detection (CAD) processor 112 coupled to the network 116 receives digital medical images from one or more of the devices 102, 106, and 110, and/or from a digitizer 115 that digitizes x-ray mammogram films 114 generated by the film mammogram acquisition device 104. For tomosynthesis data sets, an additional tomosynthesis reconstruction processor (not shown) can be coupled to the network 116 to generate and provide a plurality of tomosynthesis reconstructed image slices from x-ray tomosynthesis projection images provided by the tomosynthesis acquisition device 106. Alternatively, the additional tomosynthesis reconstruction processor can be included with or integrated into the tomosynthesis acquisition device 106. The CAD processor 112 processes the medical images according to one or more CAD algorithms and provides CAD findings associated therewith, each candidate CAD finding identifying a location of a potentially suspicious lesion in the breast and characterizing the potentially suspicious lesion by a plurality of computed features. For an x-ray tomosynthesis data volume, which comprise plurality of two-dimensional breast x-ray tomosynthesis reconstructed image slices corresponding to a respective plurality of slice depths in the breast volume, each CAD finding identifies the particular subset of the image slices spanned by a suspected anatomical abnormality, such as a potentially suspicious microcalcification cluster or a potentially suspicious mass lesion, along with the locations in each slice occupied by the suspected anatomical abnormality.

A graphical user interface implemented at a review workstation 120 displays the medical images to a viewer in accordance with one or more user interface programs carried out on a user interface processor 128, and further provides an interactive graphical user interface for displaying the CAD detection information in conjunction with the associated medical images in accordance with one or more of the preferred embodiments described further infra. Review workstation 120 comprises an interactive user interface 130 including a diagnostic display 122, an administrative display 124, and user input devices 126 (e.g., keyboard, mouse, trackball, pointers, etc) that are under the control of the user interface processor 128. Administrative display 124 is used for input and output of a wide variety of information that may be associated with a particular set of medical images (e.g., listings, tables, plots, text descriptions, etc), as well as for system installation, maintenance, updating, and related tasks. Often provided on the diagnostic display 122 at any particular time during case review by a radiologist is a two dimensional diagnostic image 132, various implementations of which are described further infra, and one or more graphical viewing and/or navigation assistance tools 136, various implementations of which are also described further infra. With particular regard to the user input devices 126 illustrated in FIG. 1, it is to be appreciated that the user interface features described herein are broadly applicable for a variety of user interface hardware implementations and that many variations are within the scope of the preferred embodiments. By way of example, whereas at least one example herein illustrates paging commands as being mouse clicks, any user input that instantiates a like paging operation (ranging from keystroke sequences to touchscreen inputs to virtual reality glove movement) is within the scope of the preferred embodiments.

Preferably, the various medical images and related information are communicated according to the DICOM (Digital Imaging and Communications in Medicine) standard and the network 110 supports the TCP/IP protocol, which is used as the transport protocol for the DICOM standard. Also coupled to the network 110 is a PACS archive 118, generally representing a repository for medical information associated with the medical imaging environment, including both current and archived images, current and archived CAD results, radiology reports for completed cases, and so forth.

The preferred embodiments described herein are seamlessly layered upon an existing CAD workflow, in which the digital or digitized medical images are processed by the CAD processor 112, and in which the medical images and their related CAD results are subsequently displayed at the review workstation 120 to a viewer, who makes a clinical determination therefrom. Although one or more of the preferred embodiments is particularly advantageous in the context of en masse breast cancer screening contexts, the clinical determination to be made by the viewer can be in relation to screening, diagnosis, follow-up, or any of a variety of other activities without departing from the scope of the preferred embodiments.

Notably, the medical imaging environment of FIG. 1 is presented by way of example only and is not intended to limit the scope of the preferred embodiments to this particular scenario. By way of example, different combinations of the devices of FIG. 1 can be placed adjacently to each other or integrated into the same hardware boxes without departing from the scope of the preferred embodiments. By way of still further example, the network 110 can be a wide-area network with the different nodes being distributed throughout a city, a country, or the world. Alternatively, and by way of still further example, some or all of the transfer of digital information can be achieved by physical transfer of disks, memory sticks, or other digital media devices without departing from the scope of the preferred embodiments. In view of the present disclosure, a person skilled in the art would be able to implement methods, systems, and/or computer program products capable of achieving the described user interfaces and processing functionalities without undue experimentation, using publicly available programming tools and software development platforms.

Figure 2:
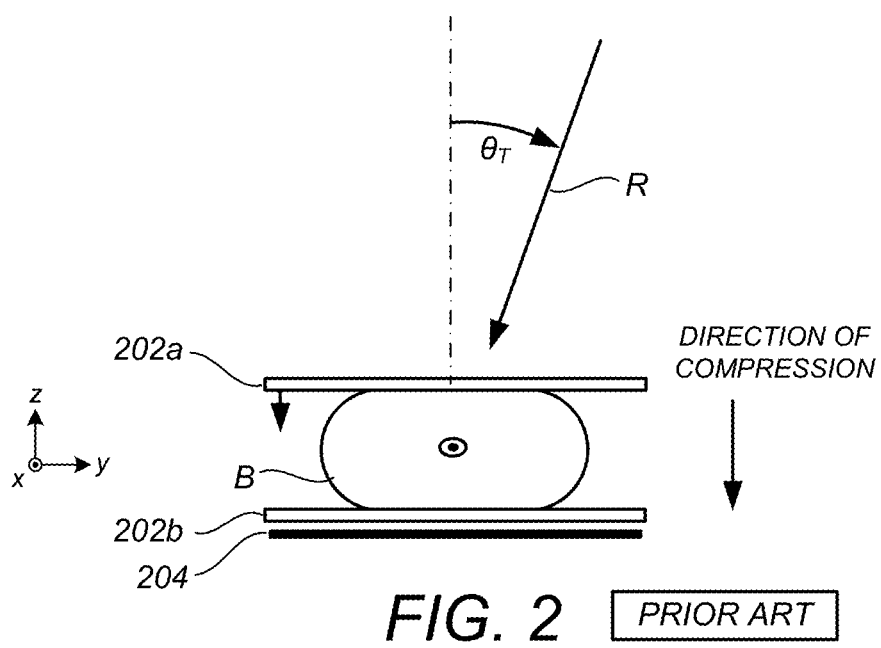
FIG. 2 illustrates a breast as compressed between two compression plates for breast x-ray tomosynthesis image acquisition.

FIG. 2 illustrates a conceptual diagram of breast x-ray tomosynthesis image acquisition, which is presented to provide a backdrop for describing certain preferred user interface features infra in the instant specification. A breast B is positioned between an upper compression paddle 202a and a lower compression paddle or platform 202b, near which is disposed an x-ray detector 204. The breast is compressed in the direction of the lower compression paddle 202b as shown, typically with a relatively large force such as 25 lbs. Each breast x-ray tomosynthesis projection image is acquired by projecting x-rays R at a respective tomosynthesis projection angle $\theta_T$ through the compressed breast B from an x-ray source (not shown) positioned on one side of the compression paddles 202a/202b (from the upper side of the compression paddles in FIG. 2) toward the x-ray detector 204 that is positioned on an opposite side of the compression paddles 202a/202b, (toward the lower side of the compression paddles in FIG. 2).

Figure 3:
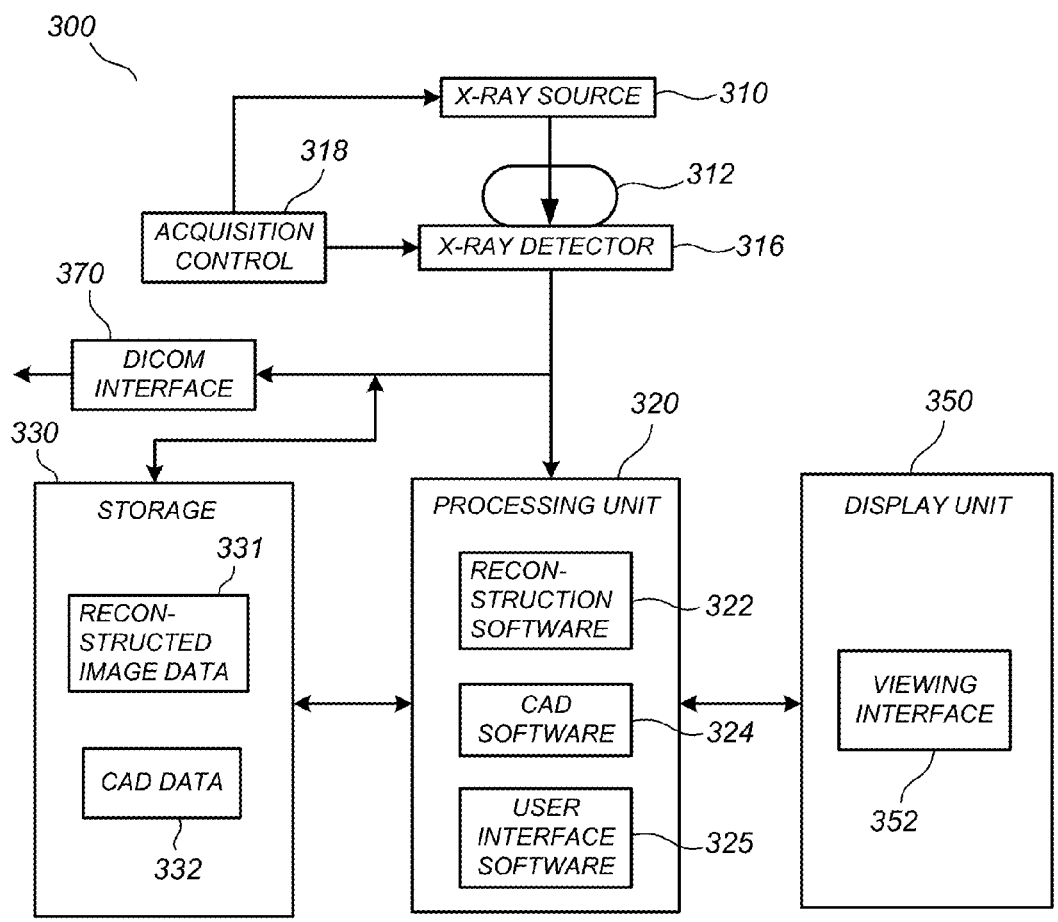
FIG. 3 a block diagram of a system in which user interface tools according to one or more preferred embodiments may be used to manage the display of breast x-ray image information.

FIG. 3 illustrates another expression of a three dimensional imaging system which may advantageously incorporate the user interface tools of the preferred embodiments. Although FIG. 3 illustrates components of a tomosynthesis system, for which the preferred embodiments are particularly advantageous, it is to be appreciated that the scope of the present teachings is not so limited and may be extended to a variety of different imaging modalities that use CAD software tools in conjunction with multi-dimensional image data.

Illustrated in block diagram form in FIG. 3 is an x-ray data acquisition unit 300 that includes an x-ray source 310 imaging a breast 312. An x-ray imager 316 such as a flat panel x-ray imager commercially available from the assignee of this patent specification generates projection image data that can be a mammogram Mp or a tomosynthesis projection image Tp. X-ray source 310 is mounted for movement so that images Tp can be taken at different angles. X-ray imager 316 can be stationary or it can also move, preferably in synchronism with movement of x-ray source 310. Elements 310 and 316 communicate with x-ray data acquisition control 318 that controls operations according to known methods. X-ray image data from imager 316 is delivered to processing unit 320. Processing unit 320 comprises reconstruction software 322, which may be stored in a computer readable medium of unit 320. The reconstruction software processes x-ray image data into Tp and Tr image data, which may be stored in storage device 330 as reconstructed data 331 and displayed at image display unit 350 as disclosed in the various embodiments described herein. Processing unit 320 further includes two dimensional and/or three dimensional CAD software 324 which processes the Tp and/or Tr data. The processing unit 320 can consist of several different physical computers, that is, the reconstruction software 322 might be resident on one computer and the CAD software 324 on a different computer, and the user interface software 325 on a third computer. CAD systems are used to assist radiologists in the interpretation of millions of mammograms per year. X-ray mammography CAD systems are described, for example, in U.S. Pat. No. 5,729,620, U.S. Pat. No. 5,815,591, U.S. Pat. No. 6,014,452, U.S. Pat. No. 6,075,879, U.S. Pat. No. 6,301,378 and U.S. Pat. No. 6,574,357, each of which is incorporated by reference herein. Application of CAD algorithms to one or more of tomosynthesis projection images and tomosynthesis reconstructed images has been proposed in U.S. Pat. No. 6,748,044 and U.S. Pat. No. 7,218,766, each of which is incorporated by reference herein.

CAD software 324 retrieves the three dimensional reconstructed data 331 from storage 330 and processes the tomosynthesis data set, generating CAD overlay images for display over each two dimensional image slice or slab. A CAD overlay image may include one or more markers which are associated with features of a corresponding image slice or slab that are suggestive of a cancerous or pre-cancerous lesions. The CAD overlay images are referred to herein as the CAD data set 332 and following generation may be stored in the storage device 330 along with the reconstructed data, for later display at the workstation, or for forwarding to an external display device, for example using DICOM (Digital Imaging and Communications in Medicine) interface 370. For example, as described in U.S. Pat. No. 6,909,795, which is incorporated herein by reference, the tomosynthesis CAD information of the present invention may fixably integrated into the pixels of a secondary image derived from a source image, and the secondary image transferred using a DICOM Secondary Capture Image Information Object Instance (SCI-IOI), either to a viewing workstation, printer or other output device.

User interface software 325 is, in one embodiment, a software module which can be loaded on any system that stores three dimensional image data for display. The interface may be used to select the number of "threshold" CAD marks to be displayed in addition to the functionality described below. The software module is stored in a computer readable medium of the system, and operable when executed upon by a processor of the system to generate an initial display which introduces the three dimensional data set to a radiologist in a manner that facilitates review of the data set. The user interface software 325 includes functionality for identifying features that correspond to a common region of interest, grouping the identified features, assigning an a group identifier to the related features, identifying an initial two dimensional image slice for display when viewing each group, and populating a user interface data structure with feature information for the three dimensional data set.

According to one aspect of the preferred embodiments, the user interface also includes several tools for improving quality and efficiency of the review of the three dimensional data set. These tools allow the user to easily select different regions of interest, identify and scroll through two dimensional slices and slabs associated with selected regions of interest and obtain enhanced views of regions of interest. With such an arrangement the efficiency and effectiveness of review is improved. It should be noted that although the user interface is described as performing different functions, the functionality may be delineated so that processing, display and/or manipulation of data may each be independently performed by any computer that has access to the image data.

Figure 4:
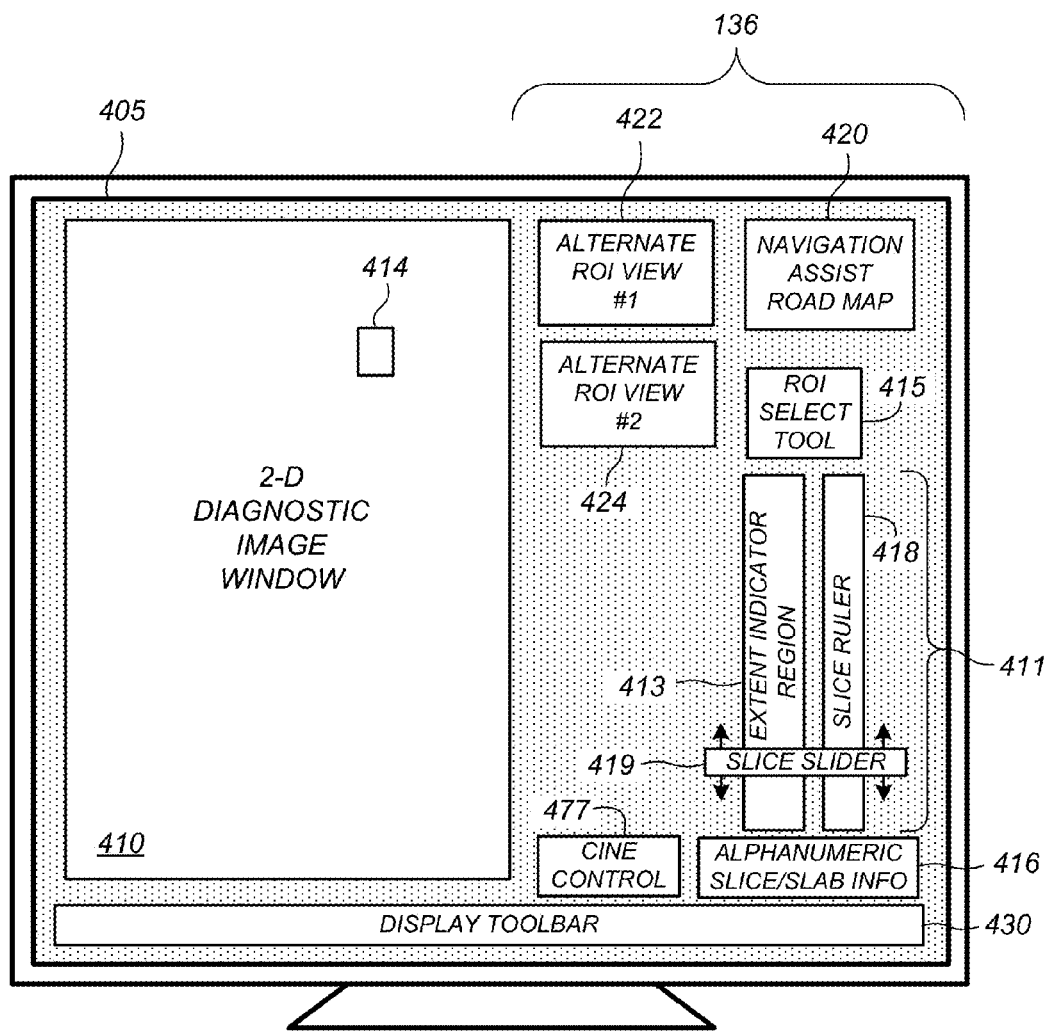
FIG. 4 illustrates a block diagram of a user display according to a preferred embodiment including exemplary positioning of certain user interface tools thereof.

FIG. 4 illustrates a block diagram of a user display according to a preferred embodiment including exemplary positioning of certain user interface tools thereof. Illustrated in FIG. 4 is a block diagram of a display 405 including a two dimensional diagnostic image display window 410, a display toolbar 430, a graphical depth navigation tool 411 (including a slice ruler 418, an extent indication region 413 and a slice slider 419), a region of interest (ROI) selection tool 415, a navigation-assisting CAD annotation road map window 420, and one or more alternate region of interest (ROI) view windows 422 and 424. The two dimensional image display area 410 is used for displaying a current two-dimensional diagnostic image to the radiologist, which will generally be a diagnostic-quality Mp image, a Tr image, a slabbed Tr image, a cine display of Tr images or slabbed Tr images, or a composited image as described further hereinbelow. The currently displayed two-dimensional diagnostic image 410 may further include one or more CAD markers 414.

According to one preferred embodiment, the size or shape of the CAD marker may be related to the size and/or shape of the detected lesion. For example, a larger marker may indicate a larger ROI, or differently shaped markers may be selected to distinguish masses from calcifications, and so forth. The display toolbar area 430 may include selectable icons that enable the user to control the displayed image; for example, by selecting different views, adjusting image contrast, displaying patient or display information or selected user interface tools such as the slice ruler 418, and so forth. Near the display toolbar area 30 may be displayed particular orientation information such as alphanumeric slice depth and slab thickness information 416 corresponding to the currently displayed diagnostic image 410.

The ROI selection tool 415, extent indication region 413, slice ruler 418, and slice slider 419 can be used to interactively control and monitor the image depth and image thickness corresponding to the currently displayed diagnostic image. As used herein in the context of x-ray tomosynthesis data volumes comprising a plurality of image slices representative of a respective plurality of slices of a breast volume having respective image depths, slabbing refers to the integration of multiple adjacent image slices (i.e., image slices corresponding to adjacent slices in the breast volume) into a single two-dimensional image. The resultant two-dimensional image, which can be termed an image slab, a slabbed image, or a thick image slice, is characterized by an image depth, which can be expressed as an average depth of its multiple component image slices, and an image thickness, which can be expressed in terms of the number of component image slices or the depthwise spatial extent of its component image slices in the breast volume. Any of a variety of methods for integrating the multiple adjacent image slices into a single slabbed image can be used, such as arithmetic averaging, maximum intensity projecting, and so forth.

In operation of the user interface provided by the display 415, the user may engage the slice slider 419 (for example, via a mouse click or the like) to scroll through the image slices of the tomosynthesis data volume. In addition, a user may select one or more visual indicators in the extent indication region to obtain one or more image slices in the ROI associated with the visual indicator. Alternatively, the user may use the ROI selection tool 415 to display a particular image slice or slabbed image associated with a particular marked CAD finding. The ROI selection tool 415 may include a pull down menu, a clickable arrow control, or any other mechanism for selecting from a set of marked CAD findings. As used herein, a marked CAD finding may alternatively be termed an ROI feature group. In one preferred embodiment, selection of a particular marked CAD finding using the ROI selection tool 415 causes a central slice of the set of slice images spanned by that CAD finding to be displayed. As used herein, the set of image slices "spanned" by a particular CAD finding is a contiguous set of image slices in the tomosynthesis data volume that are collectively occupied or "touched" by the identified anatomical abnormality, the contiguous set ranging from an uppermost image slice to a lowermost image slice. It is not required that every image slice in the spanned set contain visual evidence of the anatomical abnormality, and indeed it is quite common, as in the case of microcalcification clusters, for several image slices in a spanned set not to contain any such visual information. As the term "spanned" is used herein, the set of image slices "spanned" by a particular CAD finding can optionally include a very limited number, such as one, of "framing" or "end" image slices on the top end and bottom ends of the subset that do not themselves contain visual indications of the anatomical abnormality.

According to one preferred embodiment, a navigation-assisting CAD annotation road map window 420 is provided that includes a thumbnail or small-scale two dimensional image that displays all CAD markings for the data set. The two dimensional image may comprise an Mp image, a Tr image, a slabbed Tr image that is laterally representative of the tomosynthesis data volume, i.e., representative of the slab-shaped tomosynthesis data volume as "seen" from a viewpoint distal therefrom in a direction normal to the plane along which the breast is flattened. In one embodiment the two dimensional image is displayed with all of the CAD findings for the tomosynthesis data set. In other embodiments, the CAD findings displayed in the navigation assist window are limited to a particular number of results, or are limited by size, depth, type or other thresholding means. A reviewer may access image data associated with particular ROIs by selecting the CAD mark displayed in the navigation-assisting window 420 with which it is associated. When a CAD mark from the navigation-assisting window 420 is selected, the display is updated so that the central slice of the Tr slab associated with the CAD mark is displayed in area 410. The selected CAD mark is highlighted in the diagnostic image area 410, and the slice slider and extend marker information for the slab is provided in the area 411. It should be noted that although the navigation-assisting window 420 is shown as a thumbnail view within the same display as diagnostic image 410, it is not required that the image be so located or sized. While it is believed that it is desirable to place such a navigation window near the breast image for ease of review, it is to be appreciated that other interfaces may place such a window elsewhere on the display, or on an alternate display; such arrangements are considered to be alternate embodiments within the scope of the present teachings.

The alternate ROI view windows 422 and 424 provide enhanced images of the selected ROI. For example, in one embodiment one ROI window may provide a magnified view of the calcification, while another window provides a cluster view of the lesion. In still other preferred embodiments it is envisioned that an alternate ROI view window may display a correlated portion of an historical Mp image, to enable the reviewer to gauge any degree of change for that particular region of interest. As with the placement of the navigation-assisting window 420, although the alternate view windows 422 and 424 are shown as thumbnail views proximate to the breast image, other placements and sizing of the windows are envisioned by the present preferred embodiments.

Marked CAD findings (ROIs) may also be navigated via the extent indication region 413. As described below, the extent indication region includes a visual indicator identifying the location and extent of each marked CAD finding (ROI) in the data volume. The user interface may be configured such that selection of a particular visual indicator causes the central slice of that region of interest to be displayed in area 410. In addition, the user interface may be configured so that selection of a particular visual indicator (or alternatively, the selection of a CAD mark 414 in image area 10 or in navigation-assisting window 420) causes the alternate ROI view windows 422, 424 to display the region of interest in a magnified, cluster or other view. Also illustrated in FIG. 4 is a cine control tool 477.

FIG. 4 thus displays several different methods by which a reviewer of tomosynthesis data may navigate through the data set to examine regions of interest. It should be understood that it is not required that all of these navigation mechanisms be provided, but rather the preferred embodiments include interfaces which can include any combination of the described tools (i.e., slice slider, ROI selector, navigation assist windows, visual indicators, alternate view windows, etc.). Thus, the scope of the present teachings is not limited to any particular combination of the described user interface tools.

Figure 5:
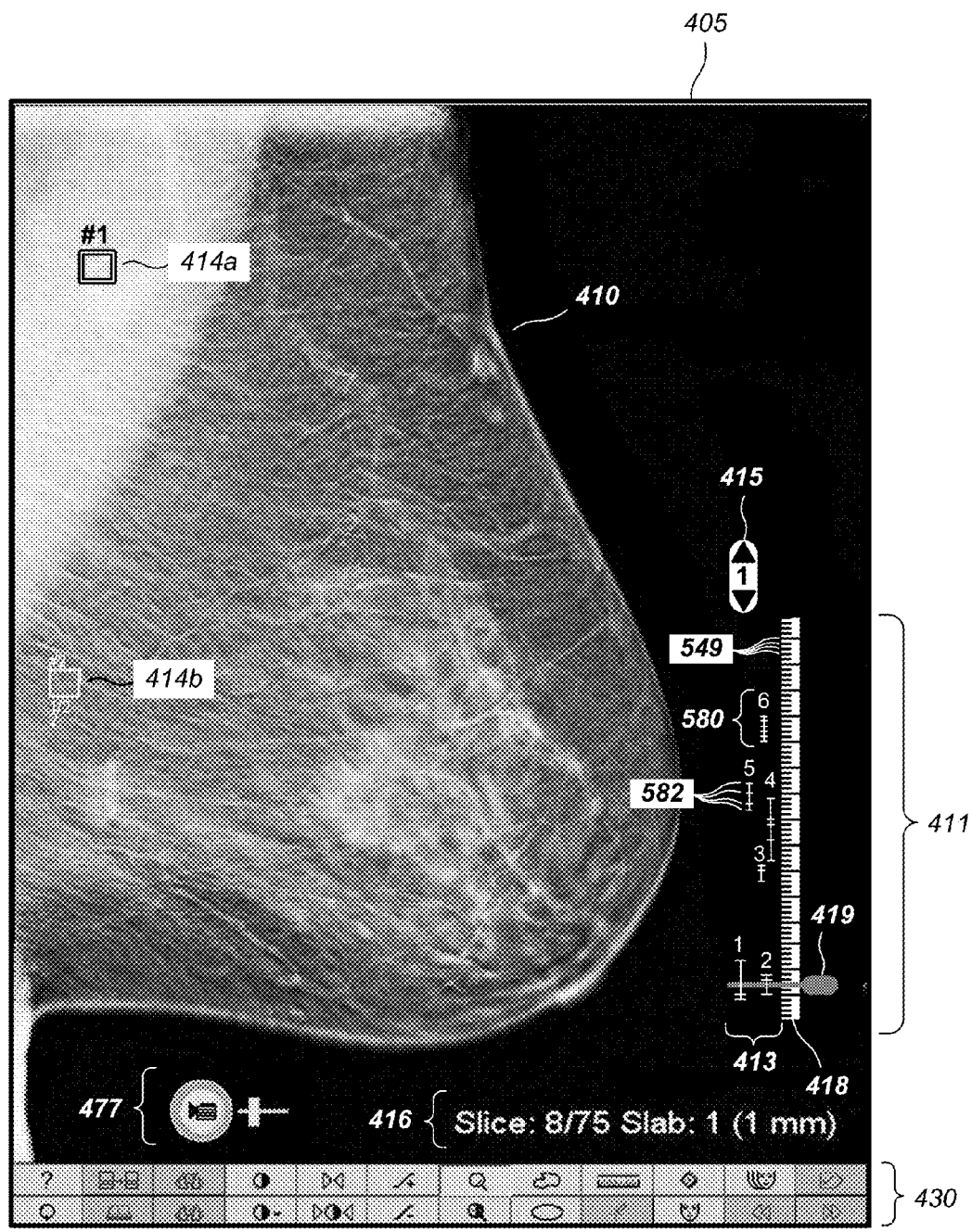
FIG. 5 illustrates an interactive user interface display according to a preferred embodiment.

FIG. 5 illustrates a closer view of the display 405 as populated with a particular diagnostic display image 410 and particular examples of interactive user interface tools according to one or more preferred embodiments. Illustrated in FIG. 5 is an exemplary display screen which includes the slice ruler 418, the slice slider 419 and the ROI selection tool 415. The slice ruler 418 includes individual hash markers 549, wherein each has marker is representative of an image slice contained in the tomosynthesis data volume.

Illustration in the extent indication region 413 are CAD indicator icons 580. As can be seen in FIG. 5, the height of each CAD indicator icon 580 is matched to depthwise spatial extent of the anatomical abnormality associated with that CAD finding, thus providing a visual indication as to the depth of the associated lesion in terms of slices. In the example of FIG. 5 there are six regions of interest denoted by six CAD indicator icons 580. Both the CAD indicator icons 580 as well as the CAD mark 414a associated with ROI #1 (CAD finding #1) are highlighted. With such an arrangement a reviewer can quickly ascertain that the lesion associated with CAD mark 414a expands through the slices indicated by the CAD indicator icon #1 as positioned against the slice ruler 418. In one embodiment, the introductory image that is presented when a case is brought up for display on the CAD system is the central slice for ROI #1, although that is not a requirement. It is to be appreciated that other introductory images, for example those associated with the largest detected mass or the region with the largest population of calcifications may be provided as introductory images, and the preferred embodiments are not limited to any particular selection of introductory image. Note in FIG. 5 that only CAD marks 414a and 414b are shown. As the slice slider moves up ruler 418, the additional CAD marks, which are associated with ROIs on 'higher' slices, become visible. Also illustrated in FIG. 5 is the cine control tool 477, which includes a slidable handle for controlling the frame rate of cine playback.

Preferably, as shown in FIG. 5, each of the CAD indicator icons 580 includes at least one single-slice highlighting mark 582. Each single-slice highlighting mark 582 is positioned on its associated CAD indicator icon 580 at a location indicative of the slice depth of a respective one of the subset of image slices spanned by the associated CAD finding that contains viewable image information corresponding to that associated CAD finding. Thus, for example, if the associated CAD finding is a microcalcification cluster that spans ten image slices but contains only four small individual microcalcifications, several of those ten image slices will not contain any visual information indicative of the microcalcification cluster. Advantageously, the single-slice highlighting marks 582 provide the user with a fast and intuitive visual description of which particular image slices will contain viewable microcalcifications. The single-slice highlighting marks 582 can also be used for highlighting prominent or important individual image slices for other types of anatomical abnormalities, such as suspicious masses. For example, for suspicious masses, there can be provided single-slice highlighting marks 582 that represent the particular image slices containing a "root" of a spiculation extending from the mass, or alternatively the single-slice highlighting marks 582 can be used to identify the image slices containing the highest-contrast cross-section of the suspicious mass. Thus, it is to be appreciated that the single-slice highlighting marks 582 can be used in the context of a variety of different types of CAD findings other than just microcalcification clusters.

Thus, illustrated in FIGS. 4-5 is a user interface display 405 associated with a computer-implemented method for processing and displaying breast x-ray tomosynthesis information according to a preferred embodiment. A plurality of two-dimensional breast x-ray tomosynthesis reconstructed image slices corresponding to a respective plurality of slice depths in a breast volume is received. A plurality of CAD findings associated with the breast volume is received, each CAD finding identifying a subset of the image slices spanned by a suspected anatomical abnormality and locations therein of the suspected anatomical abnormality. A two dimensional diagnostic image 410 is displayed that comprises either (i) a single one of said received image slices, or (ii) a plurality of depthwise adjacent ones of the received image slices slabbed together, the diagnostic image thereby being characterized by an image depth and an image thickness. Providing on the user display in visual proximity to the two dimensional diagnostic image 410 is a graphical depth navigation tool 411 configured to graphically communicate to a user the image depth and the image thickness and to allow user control thereof. The graphical depth navigation tool comprises (a) a slice ruler 418 spatially extending in a first direction (the vertical dimension in FIGS. 4-5) representative of the image depth, and (b) a slice slider icon 419 disposed along the slice ruler at a user-controllable position corresponding to the image depth. A plurality of CAD indicator icons 580 are displayed that correspond respectively to the plurality of CAD findings, each CAD indicator icon 580 running near and along the slice ruler 418 of the graphical depth navigation tool 411 and spanning a contiguous segment thereof that corresponds in depthwise position and extent to the subset of image slices spanned by the associated CAD finding. At least one single-slice highlighting mark 582 is displayed on each of the CAD indicator icons 580, each single-slice highlighting mark 582 being positioned on its associated CAD indicator icon 580 at a location indicative of the slice depth of a respective one of the subset of image slices spanned by the associated CAD finding and containing viewable image information corresponding to that associated CAD finding.

Figure 6:
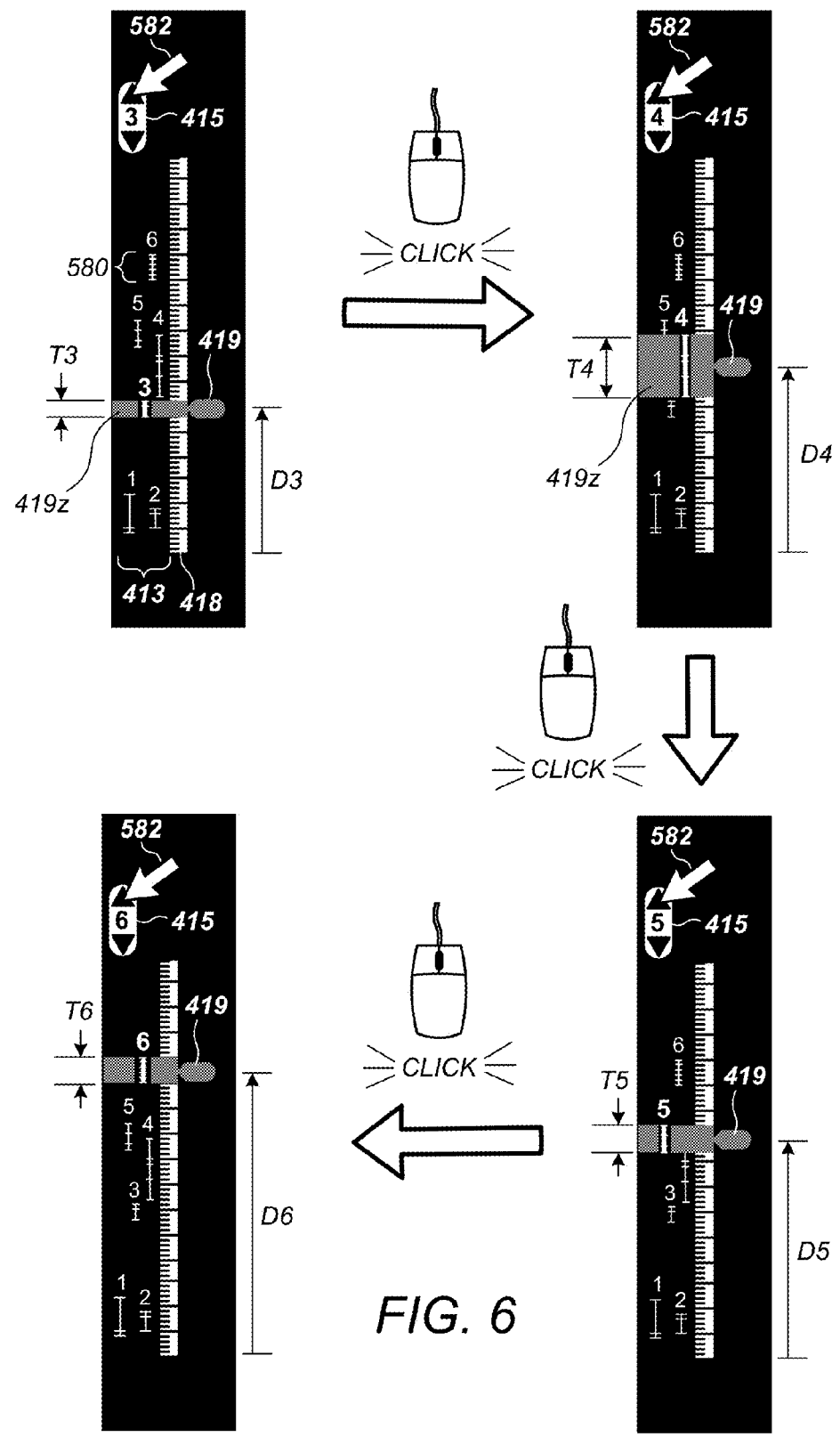
FIG. 6 illustrates a graphical depth navigation tool and CAD-assisted image navigation therewith according to a preferred embodiment.

FIG. 6 illustrates the graphical depth navigation tool 411 and ROI selector tool 415 at successive states of CAD-assisted image navigation according to a preferred embodiment. Responsive to a user selection at the ROI selector tool 415, such as by placing a mouse icon 582 thereon as shown and entering a mouse click, a next CAD finding (beginning with CAD finding #3 in FIG. 6) is established. The displayed two dimensional diagnostic image 410 is then modified to correspond to at least one image slice in the subset of image slices spanned by the currently selected CAD finding. The slice slider icon 419 includes a thickness indicator 419z that extends along the slice ruler by a distance that corresponds to the image thickness of the displayed two dimensional diagnostic image. Responsive to the user selection at the ROI selector tool 415, the slice slider icon 419 and the thickness indicator 419z are automatically adjusted to correspond to the image depth and image thickness of the modified two dimensional diagnostic image. The currently selected CAD indicator icon 580 is visually highlighted compared to the other CAD indicator icons, such as by making it brighter and/or wider. CAD annotation markings on the currently displayed two dimensional diagnostic image are updated to reflect the currently selected CAD finding. As illustrated in FIG. 6, the current location of the slice slider icon and the size of the thickness indicator 419z are automatically adjusted to correspond to the currently selected CAD finding as the user clicks through the sequence of marked CAD findings. CAD-assisted image navigation according to the preferred embodiment of FIG. 6 has been found particularly useful and effective in facilitating prompt yet thorough review of the marked CAD findings associated with the tomosynthesis data volume.

According to one preferred embodiment, the modified two dimensional diagnostic image 410 is a slabbed image formed by slabbing the subset of image slices spanned by the currently selected CAD finding, the slabbed image not including contributions from image slices not spanned by the currently selected CAD finding. According to another preferred embodiment, the modified two dimensional diagnostic image comprises a slabbed sub-image of a localized neighborhood that laterally encompasses the currently selected CAD finding (see, for example, the slabbed sub-image 1020 of FIGS. 10A-10B infra), along with a non-CAD-specific sub-image (see, for example, the area 1050 of FIGS. 10A-10B infra) encompassing substantially all areas in the modified two dimensional diagnostic image outlying that localized neighborhood. Alternatively, there can be displayed in that localized area a cine-loop sequence consisting of the subset of image slices spanned by the currently selected CAD finding. The cine-loop sequence can be shown one image slice at a time, or can alternatively comprise a sequence of slab images formed by slabbing two or more adjacent ones of the subset of image slices spanned by the currently selected CAD finding. The non-CAD-specific sub-image can consist of information taken from an actual two-dimensional mammographic image of the breast, a synthetic two-dimensional mammographic image of the breast derived from the received image slices, a single one of the received image slices, or a slabbed image formed by slabbing two or more of the received image slices.

Provided in conjunction with the option of CAD-based navigation based on the ROI selector tool 415 is a manual option in which the user can directly manipulate the slice slider icon 419 and/or the image thickness indicator 419z. The user is also provided with the option of navigating at will to any particular marked CAD finding by clicking directly on the corresponding CAD indicator icon 580, wherein the image depth and image thickness will be automatically adjusted according to the depth and spatial extent of the associated CAD finding.

Figure 7A:
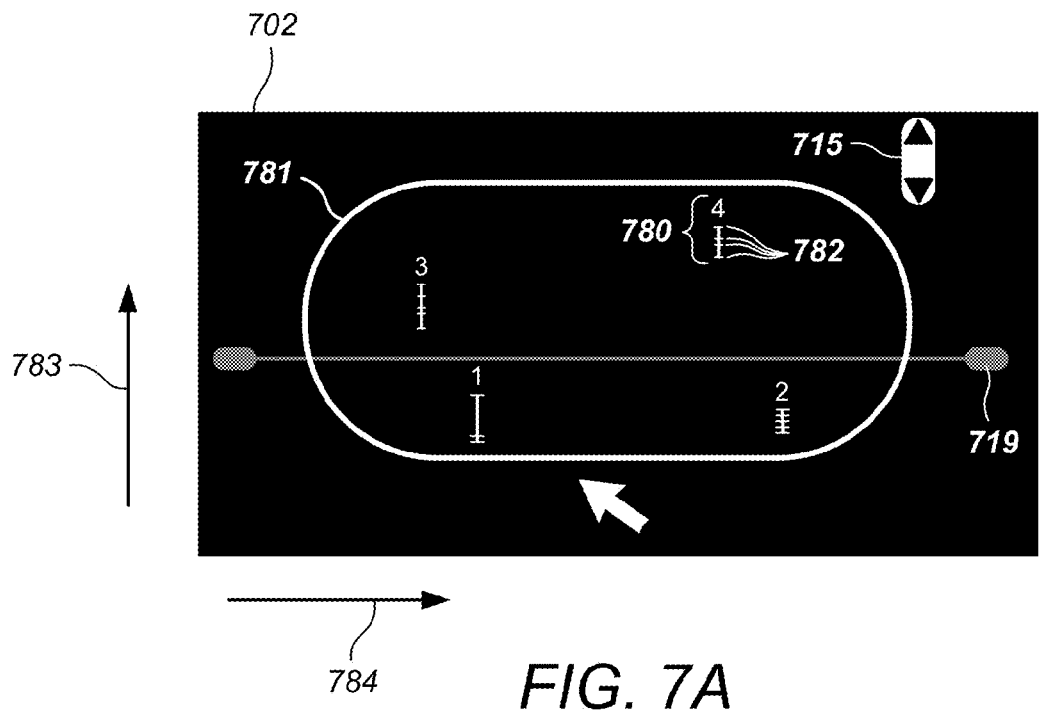
FIGS. 7A-7B illustrate a graphical depth navigation tool according to a preferred embodiment.
Figure 7B:
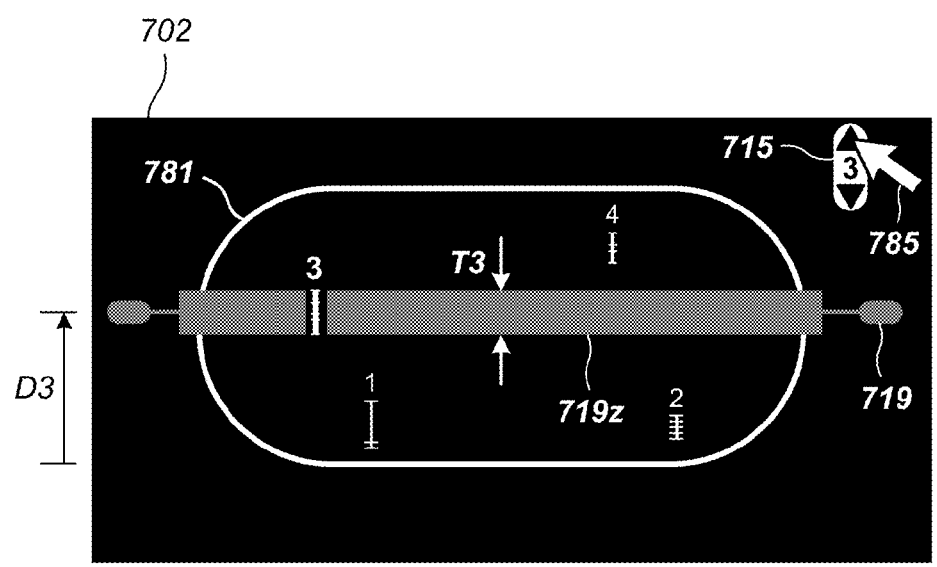

FIGS. 7A-7B illustrate a graphical depth navigation tool 702 according to another preferred embodiment, which can be used alternatively to or in conjunction with the graphical depth navigation tool 411 of FIGS. 5-6. Graphical depth navigation tool 702 comprises a two-dimensional outline image 781 in miniaturized form of the breast volume as projected onto a plane along the direction of breast compression, the two-dimensional outline image 781 having a depth dimension corresponding to the direction of compression (see arrow 783 in FIG. 7A) and a lateral dimension (see arrow 784 in FIG. 7A) normal to the depth dimension. The miniaturized two-dimensional outline image can be a strictly iconic representation of the breast outline not displaying internal breast tissue information from the received image slices, as shown in FIGS. 7A-7B, or alternatively can be an actual miniaturized projection image (not shown) derived from the received image slices.

Graphical depth navigation tool 702 further comprises a slice slider bar 719 extending across at least a portion of the outline image 781 in a direction parallel to the lateral dimension, the slice slider bar 719 having a user-controllable position in the depth dimension that corresponds to the image depth of the currently displayed diagnostic image. The slice slider bar 719 has a portion 719z with a user-controllable thickness in the depth dimension that corresponds to the image thickness of the currently displayed diagnostic image.

According to a preferred embodiment, a plurality of CAD indicator icons 780 are displayed on the outline image 781, each optionally including one or more single-slice highlighting marks 782. Each CAD indicator icon 780 is positioned on the outline image at a location representative of the location of the associated CAD finding in the breast volume, and has a position and extent in the depth dimension that corresponds to the slice depths of the image slices spanned by the associated CAD finding. In a manner analogous to the CAD-based navigation described above for FIGS. 5-6, provided on the user display a graphical region of interest (ROI) selector tool 715 that allows the user to sequence through the marked CAD findings one at a time. Responsive to user selection of the next marked CAD finding, the slice depth as reflected by the depthwise position of the slice slider bar 719 and the slice thickness as reflected by the thickness-indicating portion 719z are automatically adjusted to correspond to the next CAD finding in the sequence. The user is also provided with the option of manual navigation by direct manipulation of the slice slider icon 719 and/or the image thickness indicator 719z. The user is also provided with the option of navigating at will to any particular marked CAD finding by clicking directly on the corresponding CAD indicator icon 780, with the image depth and image thickness being automatically adjusted according to the depth and spatial extent of the associated CAD finding.

Figure 8A:
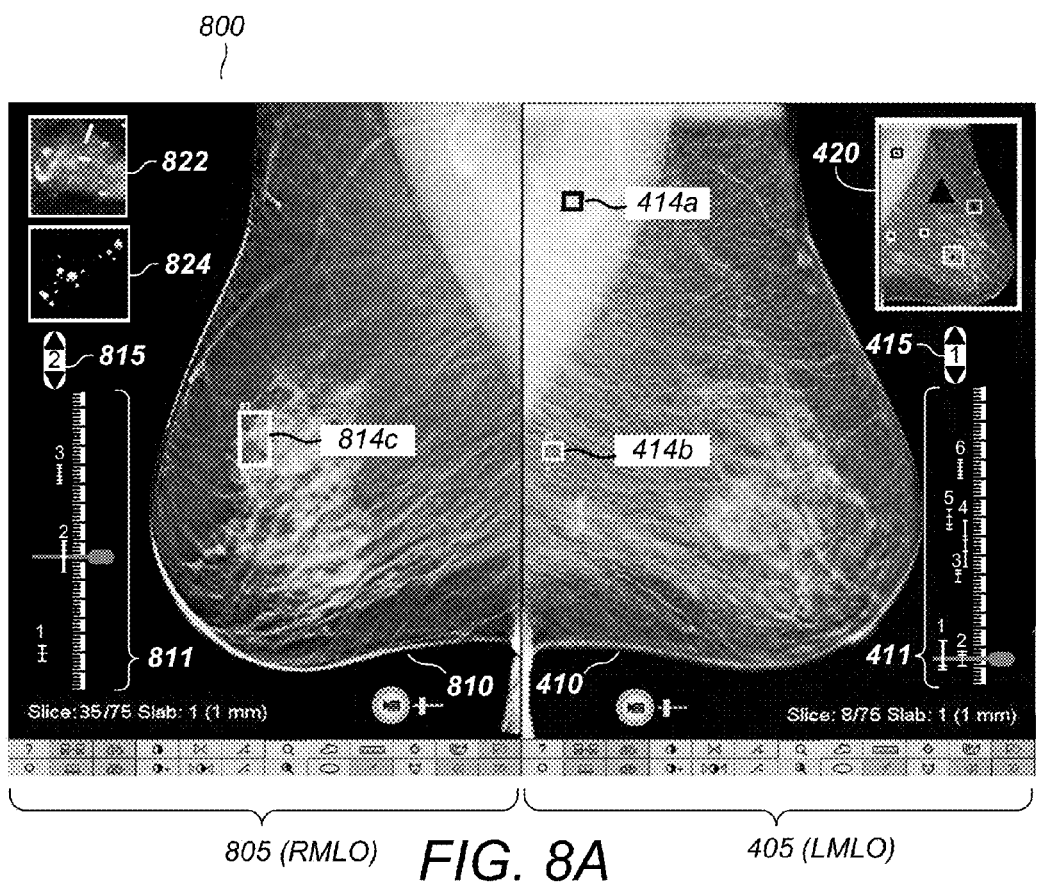
FIG. 8A illustrates an interactive user interface display according to a preferred embodiment.
Figure 8B:
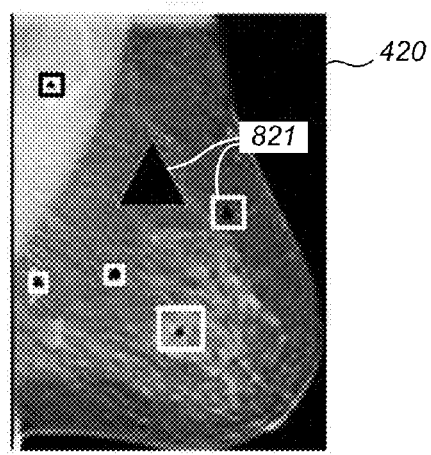
FIG. 8B illustrates a navigation-assisting CAD annotation road map window of the user interface display of FIG. 8A.

FIG. 8A illustrates an interactive user interface display according to a preferred embodiment, including a simultaneous display of right and left MLO tomosynthesis data volumes a breast in windows 805 and 405, respectively. Each view window 805/405 includes its own graphical depth navigation tool including a slice slider bar 811/411 as shown, as well as its own ROI selector tool 815/415. A navigation-assisting window 420 is shown in the upper right hand corner of the left MLO image, a close-up view of which is shown in FIG. 8B. Included in navigation-assisting window 420 are markers 821 providing a condensed, single-view CAD annotation road map for the entire data volume. The markers 821, as well as actual corresponding CAD markers 414a, 414b, and 814c shown on the diagnostic images 410 and 810 themselves, may vary in shape to indicate different types of lesions, or by size, to indicate a numeric measure not necessarily linearly related to the numeric measure. For example, some markers may be related to CAD features such as number of calcifications, or some type of CAD score such as a measure of the prominence of a combination of features representing a lesion obviousness, for example. A reviewer can quickly identify a marker 821 of particular interest and promptly and easily navigate to the slabs and associated slices by clicking on that marker 821. Such multi-dimensional visual cues and data management tools serve to increase the efficiency and effectiveness of three dimensional image review.

Figure 8C:
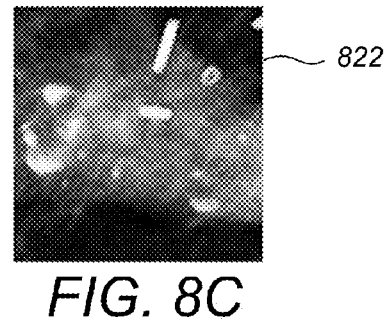
FIGS. 8C-8D illustrate auxiliary view windows of the user interface display of FIG. 8A.
Figure 8D:
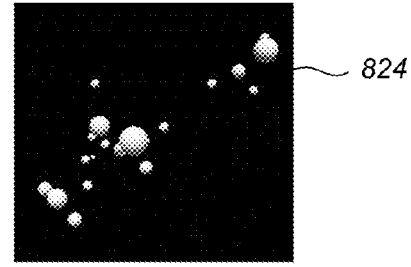

Also illustrated in FIG. 8A in the upper left hand corner of the right MLO image are alternate ROI view windows 822 and 824, close-up views of which are illustrated respectively in FIG. 8C and FIG. 8D. Alternate ROI view window 822 is a CAD finding magnification window, while alternate ROI view window 824 is a graphical three-dimensional rendering of a CAD finding. In one embodiment the alternate ROI view windows 822 and 824 are automatically associated with the currently selected CAD finding. Although these views are provided as thumbnails, it is anticipated that the user interface may be designed to include control for expanding the thumbnail view, zooming in on different areas of the thumbnail view, and so forth.

Review workflow is enhanced via the user interface tools in the following manner. The CAD tools may be invoked in a variety of ways at a variety of different points in the workflow. For example, CAD may be used as a first reader or a second reader, and may be selected using a CAD option on a control keyboard or by including the CAD function in a workflow list. The CAD algorithms execute on the data set, generating overlays for the slices that include the CAD markings. An introductory CAD marked two dimensional slice may be presented in area 410, having at least one highlighted CAD mark. Should no ROI's be identified by the CAD algorithms, an indication of such finding may be provided. Depending upon the user interface options selected, a navigation window 420 is presented with the CAD marked two dimensional slice. The ruler and depth view area are presented and populated (illustrating the extent of each ROI associated with a CAD mark), and the slice slider is automatically positioned at slice location corresponding to the displayed slice. The user may then easily step through the ROIs and associated slices to efficiently review the three dimensional data set.

Accordingly, a system and method has been shown and described that enables efficient use of CAD as a first or second reader on a tomosynthesis or other three-dimensional data set. The method described above have dealt with the ability of the user to quickly navigate to a slice/slab associated with a ROI. Sometimes it may occur that a CAD mark is provided and the reader is unable to readily discern what features of the image caused the CAD mark to be displayed.

Figure 9:
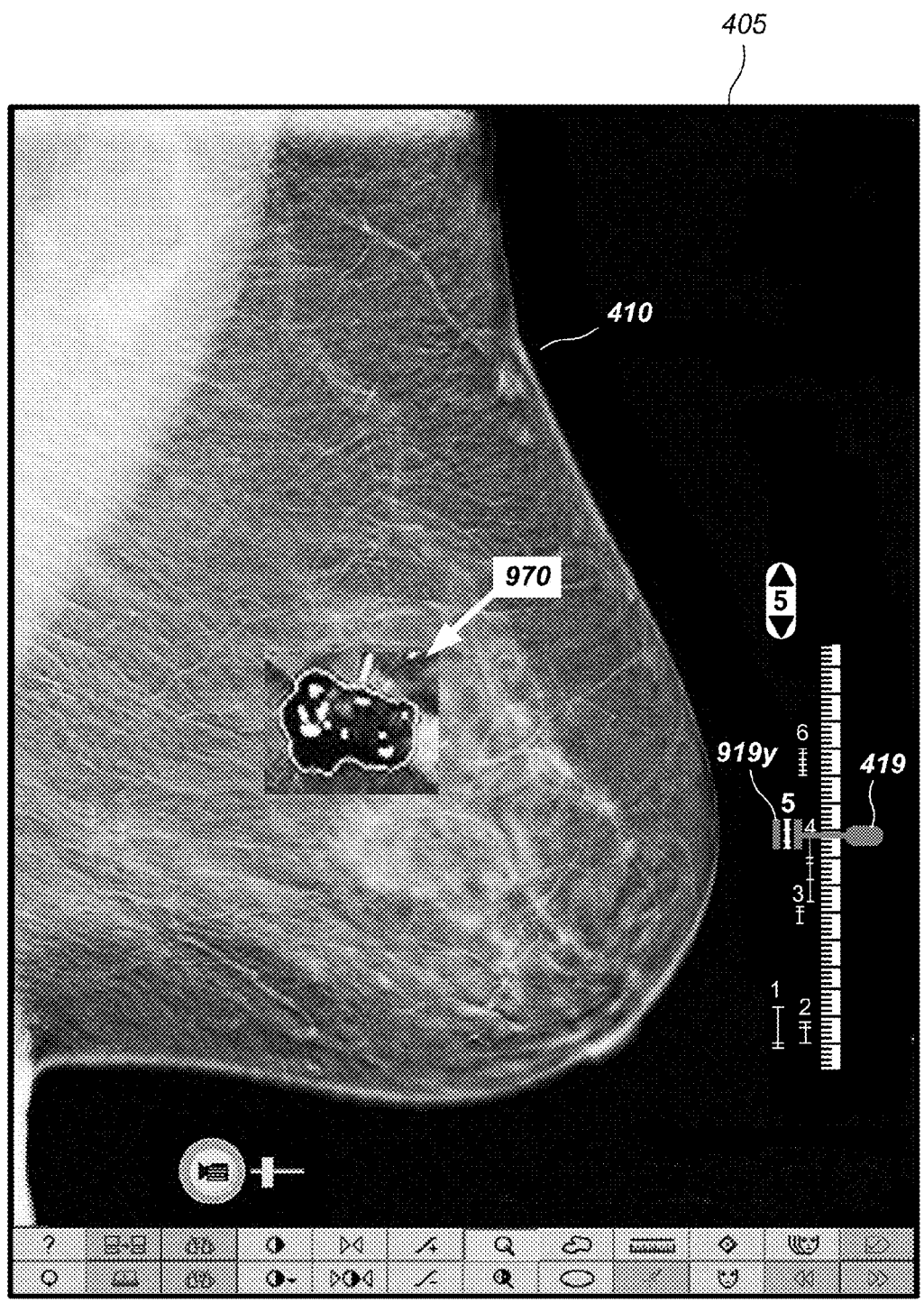
FIG. 9 illustrates an interactive user interface display including an anatomic outlining tool according to a preferred embodiment.

FIG. 9 illustrates an interactive user interface display including an anatomic outlining tool according to a preferred embodiment. Such anatomical outline tools may be invoked by a user seeking additional information regarding the operation of the CAD algorithm, and in particular it provides an understanding of what features of the image caused the CAD mark to be displayed by outlining the feature in the image and highlighting detected features or calcifications. For example, FIG. 9 illustrates a display which has invoked the anatomical outline tool for a CAD mark 970. The anatomical outline tool, for purposes of display only, modifies pixels within the affected region, dilating and highlighting individual calcifications, drawing an outline around the detected feature and coloring the interior of the mark black. Such a tool allows the radiologist to quickly identify the features in the image which caused the CAD algorithm to be interested in the region. The described user interfaces tools may support the anatomical outline tool in a variety of manners. The anatomical outline tool may be 'always on' when the slice or slab that includes the CAD mark is in the image display area 410. Alternatively, the anatomical outline tool can be automatically invoked for each respective CAD finding that is being sequenced through by the ROI selection tool 415 of FIG. 4 or the ROI selection tool 715 of FIG. 7. Alternatively, a 'dead man' switch may be provided, wherein the anatomical outline function is only enabled when a switch is actively depressed; releasing the switch causes the anatomical outline function to be disabled. Conventional methods of turning the function on or off may also be provided. The anatomical outline marking may be displayed only in the diagnostic image, or alternatively features of the anatomical outline tool may also be displayed in the alternate ROI windows 822 and 824 of FIG. 8. In one preferred embodiment, the anatomical outline tool automatically-slabs the localized area around the CAD finding according to the depthwise extent of the subset of image slices spanned by that CAD finding, and a special thickness indicator 919y is provided on the slider bar to indicate that only this localized area around the CAD finding is so slabbed.

The above-described embodiment of FIG. 4 illustrates as the diagnostic image 410 an Mp image, Tp image, or slabbed Tr image as a whole. Although the user interface tools may be advantageously used with the display of such two dimensional images, because the image is what is actually being screened by the radiologist, the composition and delineation of the image (i.e., a slice, a slab, etc.) is not a trivial matter. When user is searching for and/or evaluating micro-calcification clusters in a tomosynthesis imaging series, the review often needs to scroll back and forth between image slices, as the entire cluster is rarely visible in one slice (due to the fact that individual calcifications are quite small compared to the size of the cluster). This can be time consuming and laborious for doctors. Slab views (where multiple slices are combined either by averaging, maximum intensity projection or some other means) have been proposed as a potential solution to this problem. It is often difficult to figure out how many slices to include in the slab. According to one aspect of the preferred embodiments, slabbing is performed at CAD-detected cluster boundaries. Thus the slice-extent of each CAD-detected cluster is used to decide how many slices to slab together to optimally display the cluster to the user. For example, referring back to FIG. 5, assume that each tick mark of the ruler indicates a slice of a three dimensional image. The points next to the tick mark indicate that a feature in a feature grouping was located at the slice. It can be seen that a slice may include features that are associated with different regions of interest. The CAD indicator icon 580 indicates the slice extent of the feature group (or ROI group), that is, all of the slices within the slice extent are relevant when examining the ROI, and it is therefore desirable to slab all of the two dimensional slices for optimum review of the ROI.

Various mechanisms are envisioned for slabbing the two dimensional slices. For example the CAD tool, following execution of the CAD algorithm and generation of the marks, may make a slab image of the entire view for each CAD mark; a user would therefore review a series of pre-generated slabbed images. In another embodiment, slabbing may be done dynamically, in response to the selection of a region of interest. In still an alternate embodiment, the entire image area 410 comprises a synthesized image, populated with all of the CAD marks from the three dimensional reconstructed data set, with the regions of interest around each CAD mark being slabbed with the appropriate slices (for the cluster) at their proper location.

Figure 10A:
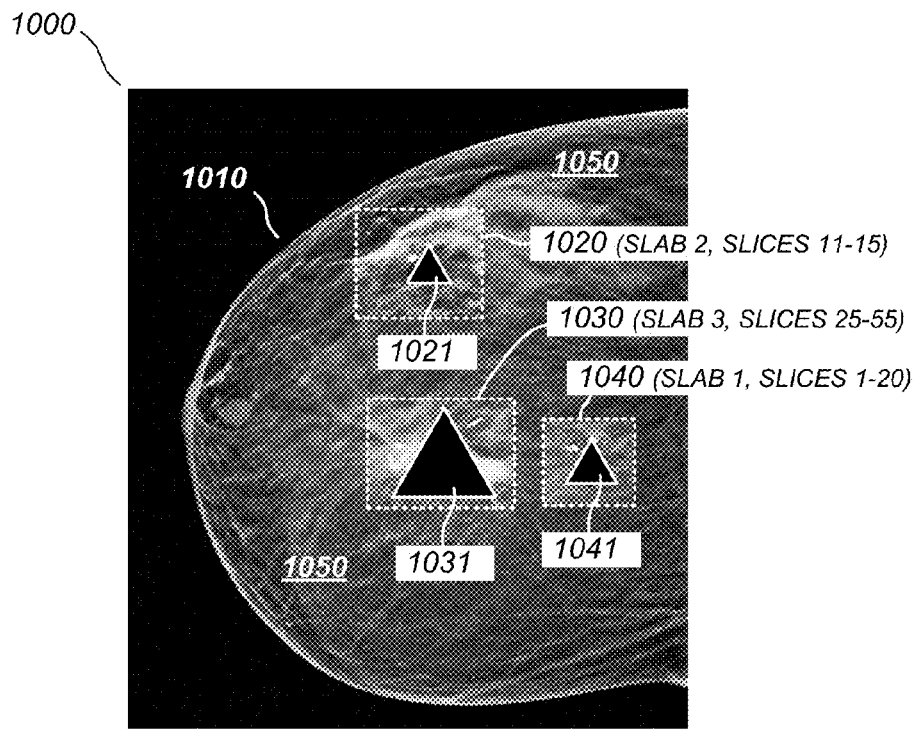
FIGS. 10A-10B each illustrate an interactive user interface display including a two-dimensional composited image having slabbed sub-images spatially localized to marked CAD findings according to a preferred embodiment.
Figure 10B:
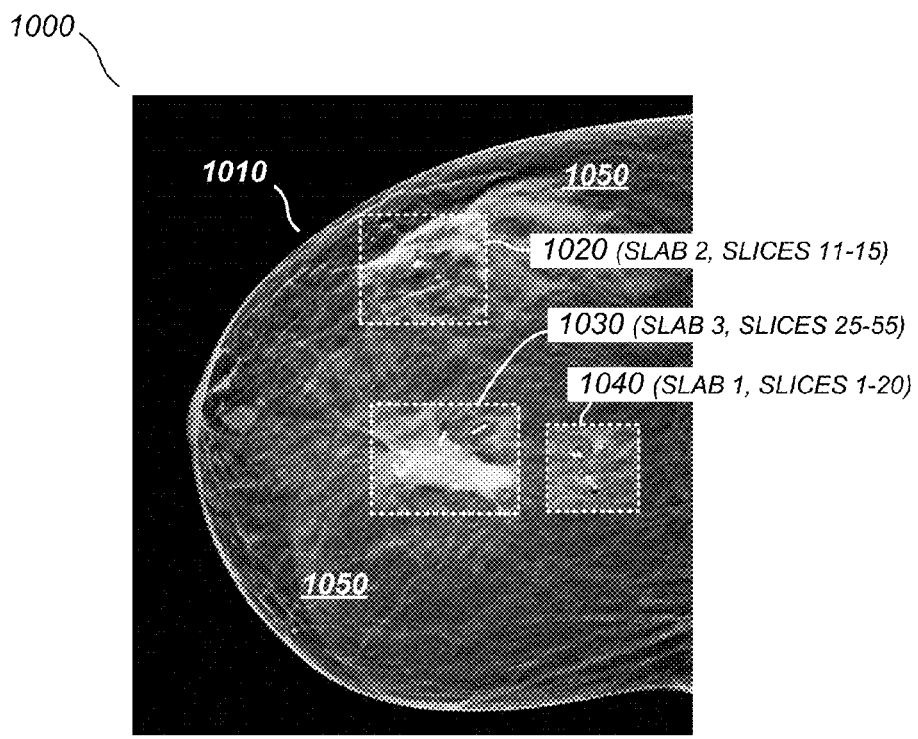

FIGS. 10A-10B each illustrate an interactive user interface display 1000 including a two-dimensional composited image 1010 having slabbed sub-images spatially localized to marked CAD findings according to a preferred embodiment. With reference to FIG. 10A, the two-dimensional composited image 1010 comprises a localized sub-image 1020 consisting of a slabbed version of slices 11-15 as windowed laterally around that locality. Similarly, a localized sub-image 1030 consists of a slabbed version of slices 25-55 in its locality, and a localized sub-image 1040 comprises a slabbed version of slices 1-20 in its locality. In the preferred embodiment of FIG. 10A, CAD marks 1021, 1031, and 1041 are displayed in superposition with the corresponding sub-images 1020, 1030, and 1040, respectively. Preferably, the remainder of the composite image 1010 outlying the areas 1020, 1030, and 1040 comprises a non-CAD-specific sub-image 1050 that can consist of information taken from an actual two-dimensional mammographic image of the breast, a synthetic two-dimensional mammographic image of the breast derived from the received image slices, a single one of the received image slices, or a slabbed image formed by slabbing two or more of the received image slices.

According to another preferred embodiment (not shown), the localized regions 1020, 1030, and 1040 can be shown one at a time in the composite image 1010, and can be successively invoked using the CAD-based navigation tools and methods of FIGS. 5, 6, 7A, and 7B supra. It should be noted that it is not necessary to display CAD marks on such a synthesized two dimensional image, but rather, as shown in FIG. 10B, the boundaries of the individual slabbed sub-images would provide a visual indication of the location of any lesion. Whichever mechanism is used, the localized slabbing along cluster boundaries is particularly advantageous in increasing the efficiency and accuracy of tomosynthesis image review.

For one preferred embodiment associated with that of FIGS. 10A-10B, the user can providing an input indicative of a cine mode request, such as by clicking on the cine control tool 477 of FIGS. 4-5. Responsive to such cine mode request, each of the sub-images 1020, 1030, and 1040 are replaced with a localized cine-loop sequence that displays the image slices (in individual or variously slabbed subsets) that are spanned by the associated CAD finding. The individual "mini-cine" sequences are each laterally windowed according to the localized neighborhood of the associated CAD finding.

It should be noted that the CAD overlay may be customized according to the desired work style of the reviewer. It is known that CAD Marks are selected to be displayed to the user by "thresholding", wherein the output of the classifier is a confidence value and any detected region above a certain confidence is allocated a mark that displayed to the user. For this reason, each image may display a different number of marks (even though the "average" number is often reported when describing the performance of the algorithm), even zero marks in some cases.

According to one aspect of the preferred embodiments, it is realized that an alternative method of selecting CAD marks for display is to always display some constant, designated number of marks per image (e.g. 5). This makes the work for the radiologist the same for each case—each case requires the review of 5 marks. Sometimes all 5 will be cancers; sometimes all 5 will be false positives. Once the designated number of marks are read, if no "cancers" are detected, the radiologist is ensured that the remaining portions of the image (whether it be a two dimensional mammogram, tomosynthesis slice or tomosynthesis slab) are be even "less suspicious"; the chance of there being cancer in other locations will be very small and not worth the time to review. Accordingly, this CAD mark display methodology can be used to increase the efficiency of review of two dimensional and three dimensional image data.

Figure 11:
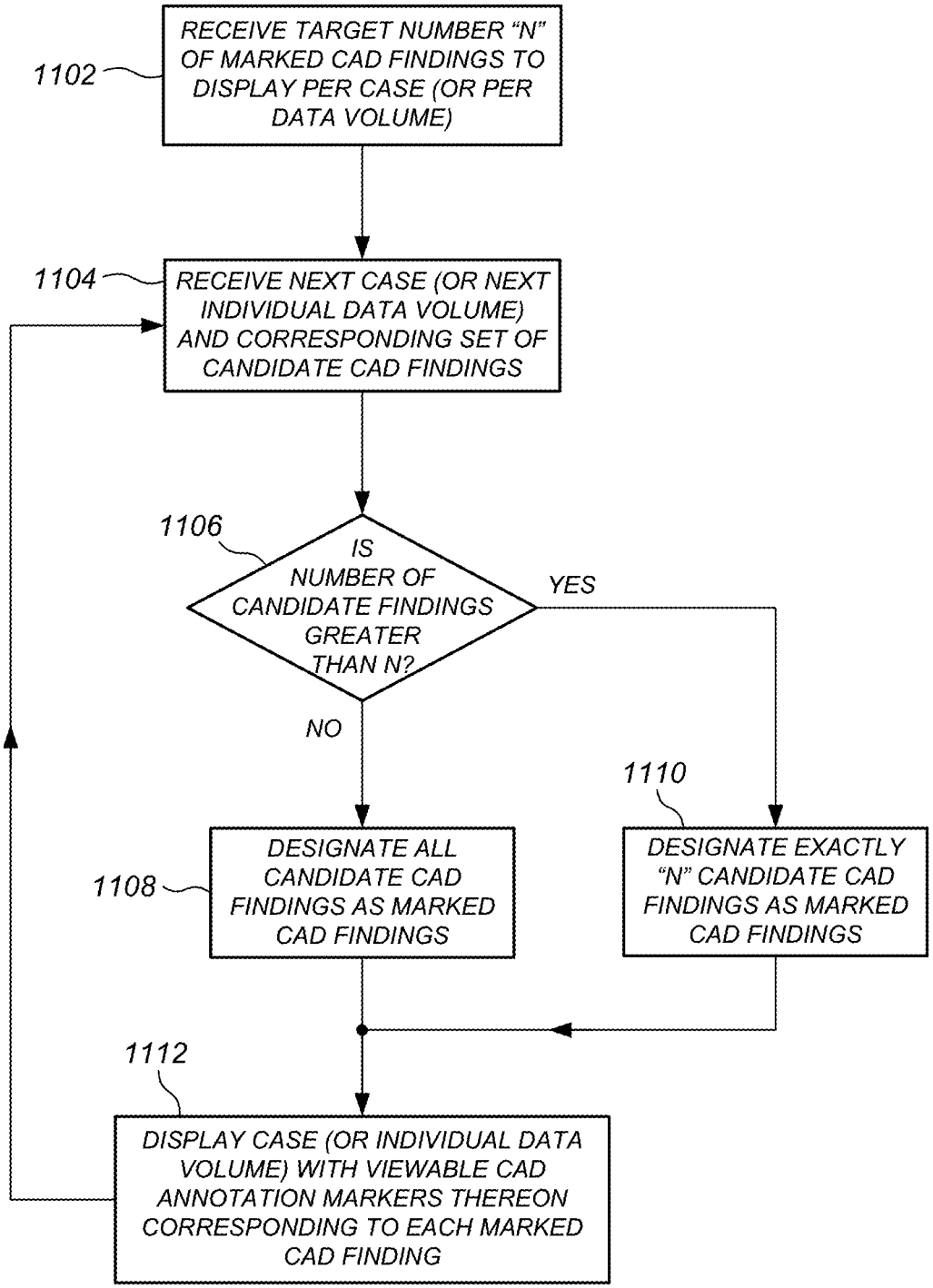
FIG. 11 illustrates selecting candidate CAD findings associated with plural x-ray tomosynthesis cases (or plural individual x-ray tomosynthesis data volumes) to mark for display according to a preferred embodiment.

FIG. 11 illustrates selecting candidate CAD findings associated with plural x-ray tomosynthesis cases (or plural individual x-ray tomosynthesis data volumes) to mark for display according to a preferred embodiment. As known in the art, a typical breast x-ray tomosynthesis case comprises multiple different views of the left and right breasts of the patient, such as left LMO, right MLO, left CC, and right CC views, each view having its own associated x-ray tomosynthesis data volume. As indicated by the parallel parenthetical expressions below, the method of FIG. 11 can be carried out on a per case basis, or on a per individual data volume basis. Generally speaking, the method of FIG. 11 is directed toward the marking of a predetermined number of candidate CAD findings per case (or per individual data volume) across all of the cases (or individual data volumes). The user experience provided is thus weighted more toward consistency in the number of marked CAD findings per case (or per individual data volume) and less toward uniform evaluation of the candidate CAD findings across the different cases (or across individual data volumes).

At step 1102, a target count "N" representing a target number of marked CAD findings to be displayed to a user on a review workstation in conjunction with a plurality of cases (or a plurality of individual data volumes) is determined, wherein that target count N is independent of any breast tissue image information contained in any of the cases (or individual data volumes). By way of example, at the beginning of a day or at the outset of any particular time interval where many cases will be reviewed, the radiologist may enter a target count "N" that can be on a per case basis or per data volume basis as desired. Alternatively, the target count "N" can be pre-specified according to a stored user profile, or according to hospital or regulatory standards, and so forth. The target count "N" is independent of any particular breast tissue image information contained in any of the data volumes that will be presented to the user.

At step 1104, a next case (or next individual data volume) is received, along with a set of candidate CAD findings associated therewith, each candidate CAD finding being associated with a potentially suspicious lesion as identified by a CAD algorithm and characterizing the potentially suspicious lesion by a plurality of computed features including a certainty of finding metric. For each case (or each individual data volume), up to the target count N of the candidate CAD findings are designated as being marked CAD findings according to the steps of, if the number of candidate CAD findings in the received set is less than or equal to the target count N as determined at step 1106, designating all of the candidate CAD findings as marked CAD findings at step 1108, and if the number of candidate CAD findings is greater than the target count N as determined at step 1106, processing the candidate CAD findings according to their computed features, including the certainty of finding metric, to designate exactly N of the candidate CAD findings as marked CAD findings at step 1110. Finally, at step 1112, the case data volumes (or the individual data volume) are (is) displayed to the user on the review workstation with viewable annotation markers thereon corresponding to each of the marked CAD findings, the review workstation not displaying annotation markers corresponding to the candidate CAD findings that are not marked CAD findings.

When the target count "N" is specified on a per case basis and the case involves multiple data volumes, a variety of different strategies for distributing the marked CAD findings among the multiple data volumes can be used and would be apparent to a person skilled in the art in view of the instant specification. Thus, for example, if the number of candidate CAD findings in each component data volume of a case is greater than "N", the designation step 1110 can comprise allocating similar numbers of marked CAD findings to each of the data volumes. Alternatively, the top "N" CAD findings as determined according to the computed features can be selected, regardless of how they are distributed among the component data volumes. As another alternative, if the number of candidate CAD findings in each component data volume of a case is greater than "N", the designation step 1110 can comprise allocating similar numbers of marked CAD findings to each of the left and right breasts.

Figure 12:
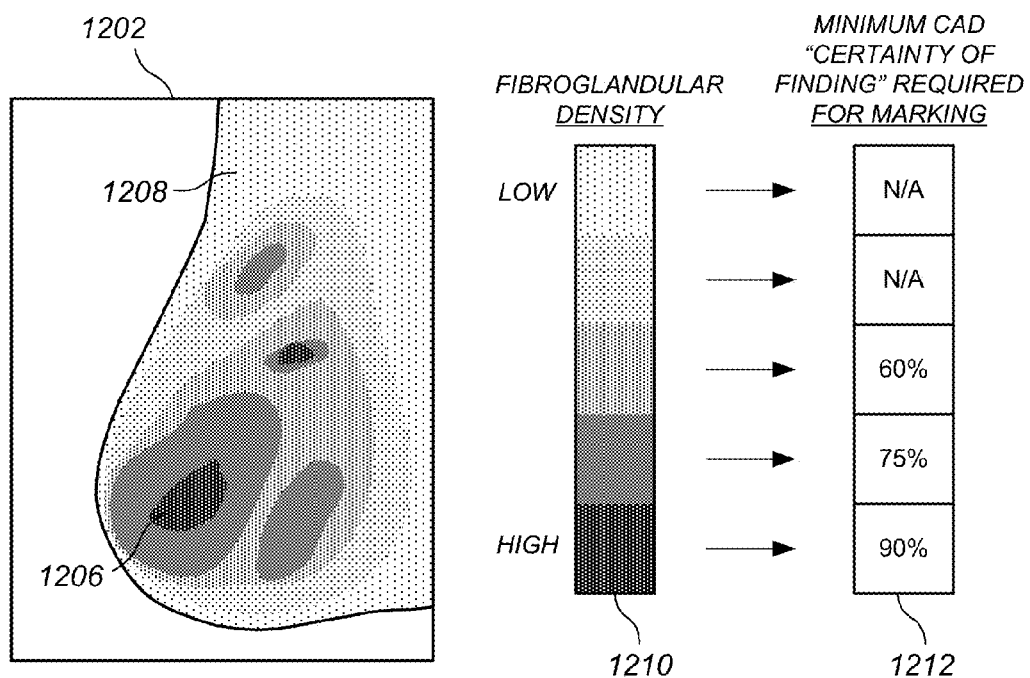
FIG. 12 illustrates a fibroglandular tissue density map and associated certainty-of-finding thresholds for designating candidate CAD findings as marked CAD findings according to a preferred embodiment.

FIG. 12 illustrates a fibroglandular tissue density map and associated certainty-of-finding thresholds for designating candidate CAD findings as marked CAD findings versus unmarked CAD findings according to a preferred embodiment. Notably, the preferred embodiment of FIG. 12 (as well as that of FIG. 13 below) are applicable for both two-dimensional x-ray mammography and breast x-ray tomosynthesis. For the particular context of two-dimensional x-ray mammography in a DICOM-based or DICOM-compliant environment, one example of a certainty of finding metric that can be used in conjunction with the currently described methods is the "Certainty of Finding" content item (code scheme designator DCM, Code Value 111012) from the Mammography CAD Structured Report Information Object Instance (Mammography CAD SR-IOI) that is used to describe and communicate the set of CAD findings for a case. Further information on this content item (111012, DCM, "Certainty of Finding") can be found in the publication "PS 3.16-2009 Part 16: Content Mapping Resource," National Electrical Manufacturers Association (2009), which is incorporated by reference herein. Similar certainty of finding metrics exist for breast x-ray tomosynthesis CAD and can be used in conjunction with the described methods. It is to be more generally appreciated that any CAD-computed data item that is numerically and/or symbolically representative of a degree of confidence or certainty that a CAD finding is indeed what the CAD algorithm reports it to be can be used as the certainty of finding metric, regardless of the particular nomenclature used to describe that metric.

Notably, as would be readily understood by a person skilled in the art, a CAD-computed certainty of finding metric is different than a CAD-computed probability of malignancy metric, as they represent generally independent concepts. By way of simplified explanation, a CAD algorithm may identify the presence of a particular mass in the breast, and may characterize that mass as relatively benign (a low probability of malignancy metric), but the CAD algorithm may have a very high degree of certainty about its conclusion that it has indeed found a mass (a high certainty of finding metric). By way of further simplified explanation, a CAD algorithm may identify the presence of a microcalcification cluster with a relatively low degree of certainty that it is really "looking at" a microcalcification cluster (a low certainty of finding metric), but the CAD algorithm may conclude that it is a particularly bad one (high probability of malignancy) if it really is a microcalcification cluster.

One example of a fibroglandular tissue density metric that can be used in conjunction with the presently described preferred embodiments is a so-called "$H_{int}$" metric described in a book by Ralph Highnam and Michael Brady entitled *Mammographic Image Analysis*, Kluwer Publishers, Boston Mass. (1999) that describes how to correct and remove the effects of x-ray scatter, x-ray energy (kVp), exposure (mAs) and breast thickness. See also their PCT Publication WO00/52641A1, which is incorporated by reference herein. The result is a completely physical description of the breast in terms of thickness and type of material—fat or fibroglandular tissue. Their interest is in the fibroglandular or "interesting" tissue and thus they call this description $H_{int}$, which is expressed in units of centimeters, and which represents the cumulative vertical height of fibroglandular tissue above any particular pixel image between the compression plates, the remaining vertical height representing "non-interesting" tissue, which is primarily fat. Other examples of suitable fibroglandular tissue density metrics are discussed in Alonzo-Proulx, et. al., "Validation of a Method for Measuring the Volumetric Breast Density from Digital Mammograms," Phys. Med. Biol. 55, pp. 3027-3044 (2010), which is incorporated by reference herein.

According to one preferred embodiment, a computer-implemented method for processing and displaying information associated with breast x-ray images is provided, wherein localized breast fibroglandular tissue density information is used together with certainty-of-finding information as a basis for selecting which candidate CAD findings to designate as marked CAD findings. In one preferred embodiment, referring briefly back to FIG. 1, the original set of candidate CAD findings is generated by the CAD processor 112 and provided as one or more DICOM CAD structured reports, whereas the designation of marked versus unmarked CAD findings is carried out a distinct review workstation 120. The relevant breast density computations can be carried out be either the CAD processor 112 or the review workstation 120. For one preferred embodiment in which the breast density computations are carried by the review workstation 120, there is advantageously provided a standalone, segregable capability in which the review workstation 120 can be programmed to carry out the methods of FIGS. 12-14 herein and be provided by a first manufacturer, whereas the CAD processor 112 can be a pre-existing device provided by a second equipment manufacturer having no sense of the methods described herein with respect to FIGS. 12-14.

Preferably, a medical x-ray image of a breast, which can be either a two-dimensional Mp image or a tomosynthesis data set in different preferred embodiments, is received along with a set of candidate CAD findings, each candidate CAD finding identifying a location of a potentially suspicious lesion in the breast and characterizing the potentially suspicious lesion by a plurality of computed features including a certainty of finding metric. A fibroglandular tissue density map of the breast based on the medical x-ray image is generated. The fibroglandular tissue density map 1202 characterizes each location in the medical image by a fibroglandular tissue density metric representative of an absolute proportion, by volume, of fibroglandular breast tissue in a local neighborhood of that location, with one example being based on the above-described $H_{int}$ metric. Each of the candidate CAD findings is designates as being either a marked CAD finding or a non-marked CAD finding based on its associated certainty of finding metric and the fibroglandular tissue density metric at the location thereof. The medical x-ray image is then displayed to a user on a review workstation with viewable annotation markers thereon corresponding to each of the marked CAD findings, the review workstation not displaying annotation markers corresponding to the non-marked CAD findings.

Preferably, as indicated graphically in FIG. 12 by a fibroglandular density legend 1210 placed next to a table 1212 setting forth associated certainty of finding thresholds, the designating is carried out such that, in order to be designated as marked CAD findings, candidate CAD findings at locations of higher fibroglandular tissue density, such as in region 1206, require higher certainties of finding than is required for candidate CAD findings at locations of lower fibroglandular tissue density, such as in region 1208. Especially when programmed on a review workstation functionally and/or commercially segregated from a CAD processor as described above, a substantial amount of value is added to the CAD workflow, because it is now "harder" to display a CAD finding when that CAD finding has a higher chance of being occluded by high localized fibroglandular density in the breast, and "easier" to display a CAD finding when it is less occluded by localized fibroglandular density.

Figure 13:
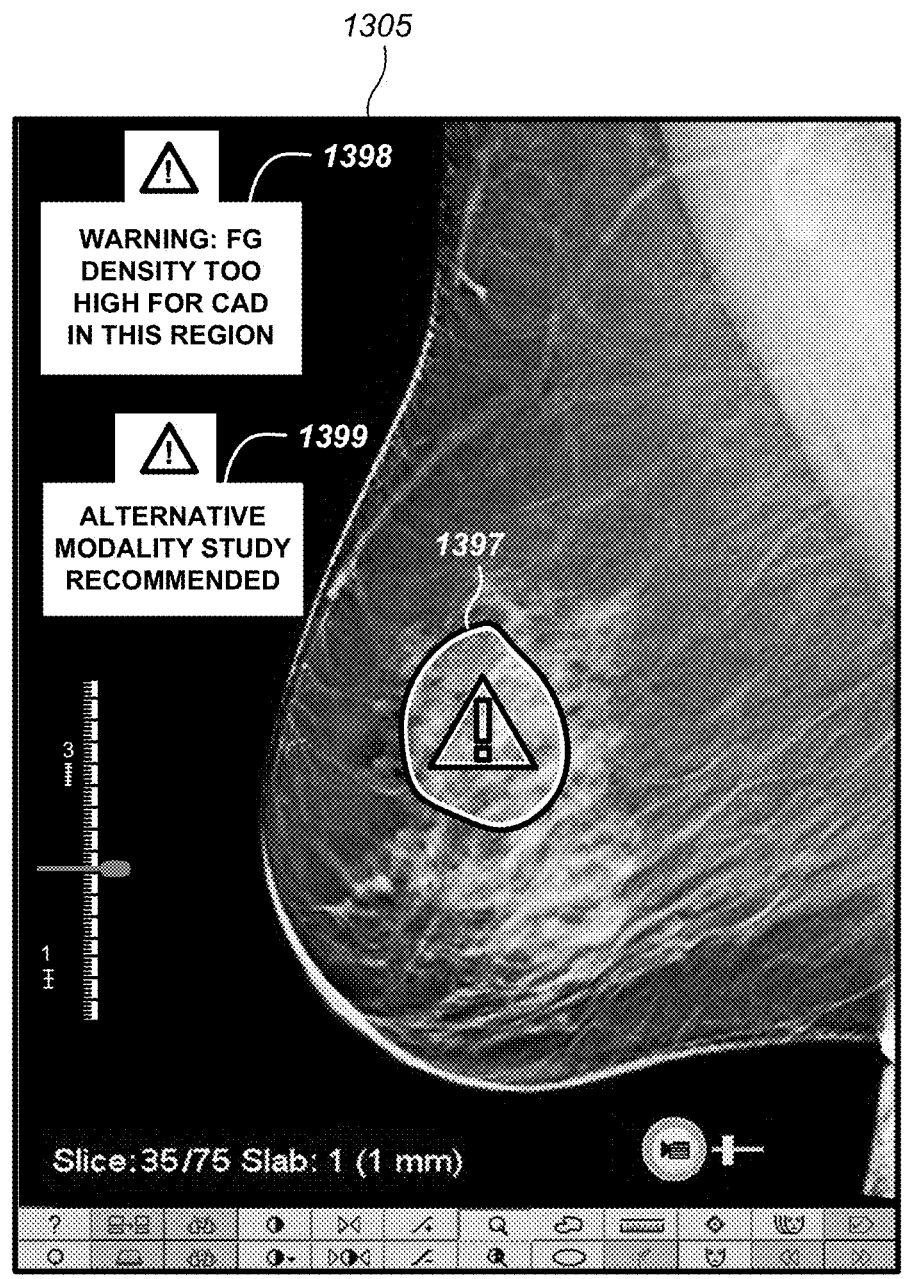
FIG. 13 illustrates an interactive user interface display including a CAD validity warning and an alternative modality recommendation triggered by an identification of a region of excessive localized fibroglandular tissue density according to a preferred embodiment.

FIG. 13 illustrates an interactive user interface display according to a preferred embodiment that also relates to the fibroglandular tissue density map 1202 of FIG. 12. In one preferred embodiment, the fibroglandular tissue density map 1202 is processed to detect a contiguous region of the breast characterized by (i) a fibroglandular tissue density metric that is higher than a predetermined statistical threshold, and (ii) a size and shape that is sufficient to substantially obscure an anatomical abnormality among the high fibroglandular density tissue therewithin. Such a size and shape might be, for example, a disk having a diameter of 1-2 cm for two-dimensional mammograms, or a spheroid having a diameter of 1-2 cm for tomosynthesis data volumes. For such a detected region, which can be termed a region of excessive fibroglandular tissue density, all of the candidate CAD findings located therein are designated as unmarked CAD findings regardless of their type or computed features. Preferably, as indicated in FIG. 13, the region of excessive fibroglandular tissue density is identified by a highlighted marking 1397, and a CAD validity warning 1398 is displayed to the user indicating that the area 1397 is too dense for reliable CAD evaluation to occur. Optionally, an alternative modality recommendation 1399 is provided that recommends an alternative imaging modality for the breast, such as breast ultrasound or breast MRI.

When the medical x-ray image is a two-dimensional x-ray mammogram, it has been acquired with the breast in a compressed state between two generally parallel compression paddles by projecting x-rays through the compressed breast from an x-ray source positioned on one side of the compression paddles toward an x-ray detector positioned on an opposite side of the compression paddles. For these cases, the fibroglandular tissue density map 1202 is a two-dimensional volumetric breast density (VBD) map computed from the two-dimensional x-ray mammogram according to a predetermined VBD computation algorithm, the VBD map containing, for each location in the x-ray mammogram, information representative of an absolute cumulative height of the fibroglandular breast tissue and an absolute cumulative height of non-fibroglandular breast tissue in a correspondingly located column of breast tissue extending between the compression paddles.

Figure 14A:
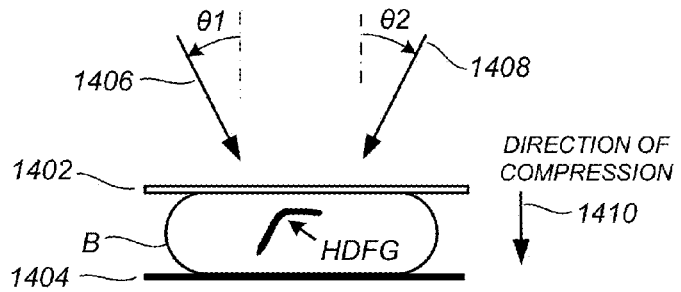
FIGS. 14A-14B illustrate a conceptual diagram of forming a three-dimensional fibroglandular tissue density map from a plurality of x-ray tomosynthesis projection images according to a preferred embodiment.
Figure 14B:
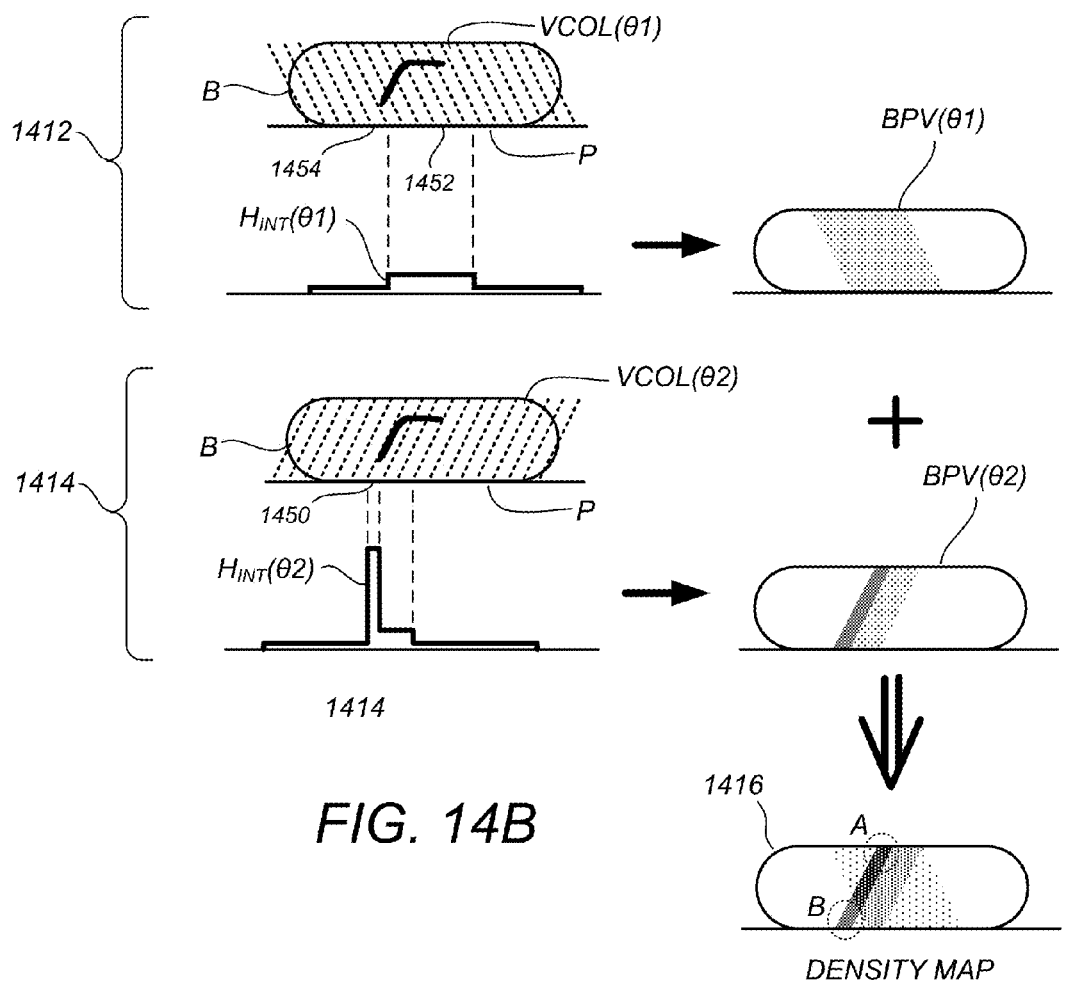

FIGS. 14A-14B illustrate a conceptual diagram of forming a three-dimensional fibroglandular tissue density map from a plurality of x-ray tomosynthesis projection images according to a preferred embodiment. When the medical x-ray image is a breast x-ray tomosynthesis volume, computed from a plurality of x-ray tomosynthesis projection images. As illustrated in FIG. 14A, each projection image is acquired with the breast B in a compressed state between two generally parallel compression paddles 1402 and 1404, each projection image being acquired by projecting x-rays R at a respective tomosynthesis projection angle (such as θ1 and θ2) through the compressed breast from an x-ray source positioned on one side of the compression paddles toward an x-ray detector positioned on an opposite side of the compression paddles, the breast x-ray tomosynthesis volume comprising a plurality of two-dimensional breast x-ray tomosynthesis reconstructed image slices corresponding to a respective plurality of slice depths in the breast volume. For these cases, fibroglandular tissue density map 1202 is a three-dimensional map computed from at least two of the x-ray tomosynthesis projection images. More specifically, each tomosynthesis projection image is processed to compute therefrom a respective two-dimensional volumetric breast density (VBD) map according to a predetermined VBD computation algorithm, the VBD map containing, for each location in the projection image, information representative of an absolute cumulative height of the fibroglandular breast tissue and an absolute cumulative height of non-fibroglandular breast tissue in a correspondingly located column of breast tissue extending between the compression paddles at the associated tomosynthesis projection angle (see, for example, the voxel columns VCOL(θ1) and VCOL(θ2) in FIG. 14B overlying a pixel location P). The at least two VBD maps are then processed to generate the three-dimensional fibroglandular tissue density map. The three-dimensional fibroglandular tissue density map can be formed, for example, backprojecting each VBD map into three-dimensional space and accumulating the results, and/or by processing the VBD maps according to a tomosynthesis reconstruction algorithm.

As illustrated by the conceptual flow diagrams 1412 and 1414 of FIG. 14B relative to a high-density subvolume HDFG in the breast, the use of such three-dimensional fibroglandular tissue density map advantageously allows for higher sensitivity for image regions having a lower $H_{int}$ for a greater number of tomosynthesis projection angles. Illustrated in FIG. 14B is a simplified example of the "fibroglandular tissue columns" or "$H_{int}$ columns" that are "seen" by incident radiation at two projection angles. The region "A" shown on the resultant fibroglandular density map 1416 is highly occluded by virtue of the extended presence of region HDFG in the voxel column above pixel 1450 at projection angle θ2, and this is not fully "cured" by the information received at pixel 1452 at projection angle θ1 because there is some amount of region HDFG in that voxel column as well. A resultant high density map value and associated high certainty of finding marking threshold is brought about for the region "A". On the other hand, although the region "B" is also highly occluded by virtue of the extended presence of region HDFG in the voxel column above pixel 1450 at projection angle θ2, this occlusion is comparatively "cured" by the information received at pixel 1454 at projection angle θ1 because there is a "clear shot" to that location from angle θ1. The region "B" thereby has a lesser resultant density map value, and a correspondingly lesser certainty of finding marking threshold, than for the region "A."

Having described exemplary embodiments, it can be appreciated that the examples described above are only illustrative and that other examples also are encompassed within the scope of the appended claims. Elements of the system and method are embodied in software; the software modules of the preferred embodiments have been described to be stored in a computer readable medium and operable when executed upon by a computer processing machine to transform information from two dimensional slice images into a displayable representation of the third dimension of the feature. Several advantages are gained by this transformation; for example, the time needed to review large sets of image data to detect potential cancerous lesions can be reduced and the accuracy with which a large image data set is reviewed is increased. As such, the preferred embodiments fill a critical need in the art to ensure that diagnostic screening is performed with efficiency and accuracy.

It should also be clear that, as noted above, techniques from known image processing and display methods such as post-production of TV images and picture manipulation by software such as Photoshop from Adobe, can be used to implement details of the processes described above. The above specific embodiments are illustrative, and many variations can be introduced on these embodiments without departing from the spirit of the disclosure or from the scope of the appended claims. For example, elements and/or features of different illustrative embodiments may be combined with each other and/or substituted for each other within the scope of this disclosure.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, while the target count "N" of marked CAD findings is described above with respect to the preferred embodiment of FIG. 11 supra, as being a single number, at least one alternative preferred embodiment exists in which the target count "N" can be a desired range of numbers, wherein at least some of the marking decisions can be based on absolute, rather than relative, confidence of finding metrics within any particular case or data volume. Therefore, reference to the details of the preferred embodiments are not intended to limit their scope, which is limited only by the scope of the claims set forth below.

What is claimed is:

1. A computer-implemented method for processing and displaying information associated with breast x-ray images acquired with an imaging device, the method comprising:
   receiving a plurality of two-dimensional breast x-ray tomosynthesis reconstructed image slices corresponding to a respective plurality of slice depths in a compressed breast volume;
   receiving a plurality of computer-aided detection (CAD) findings associated with the breast volume, each CAD finding identifying a subset of the image slices spanned by a suspected anatomical abnormality and locations therein of the suspected anatomical abnormality;
   displaying on a user display a two dimensional image comprising a single one of the received image slices or a plurality of depthwise adjacent ones of the received image slices slabbed together;
   displaying a navigation tool on the user display in visual proximity to the two dimensional image, the navigation tool comprising:
      an outline in miniaturized form of the breast volume, the outline having a depth dimension corresponding to a direction of compression and a lateral dimension normal to the depth dimension,
      a plurality of CAD indicator icons displayed within the outline, the plurality of CAD indicator icons corresponding to respective CAD findings and being positioned at respective locations representative of respective associated CAD findings in the breast volume, and
      a slice slider bar extending across at least a portion of the outline, a first portion of the slice slider bar being controllable by the user in the depth dimension to select the image depth, a second portion of the slice slider having an adjustable thickness corresponding to the image thickness of the currently displayed image.

2. The method of claim 1, the outline being an iconic representation of the breast outline while not displaying internal breast tissue information from the received image slides.

3. The method of claim 1, the outline being a miniaturized projection image derived from the received image slices.

4. The method of claim 1, wherein the plurality of CAD indicator icons are displayed on the outline.

5. The method of claim 1, each CAD indicator comprising at least one highlight mark representing a single slice.

6. The method of claim 5, wherein the anatomical abnormality identified by a first of the CAD findings is a microcalcification cluster, and respective highlight marks on the associated CAD indicator icon identify image slices spanned by the microcalcification cluster that contain a viewable individual microcalcification in that microcalcification cluster.

7. The method of claim 1, the slice thickness reflected by the thickness of the second portion of the slice slider being automatically adjusted.

8. The method of claim 7, the thickness of the second portion of the slice slider being automatically adjusted in response to selection of a marked CAD finding by the user.

9. The method of claim 1, wherein the second portion extending across the outline in a direction parallel to the lateral dimension and the slice slider bar has a portion with a use-controllable thickness in the depth dimension that corresponds to the image depth of the currently displayed image.

10. The method of claim 1, further comprising displaying a slice ruler extending in the depth dimension, the slice ruler comprising individual markers representing an image slice contained in the breast volume.

11. The method of claim 1, further comprising a graphical region of interest (ROI) selector tool positioned in visual proximity to the two dimensional image and the navigation tool, the ROI selector tool allowing the user to select the CAD findings one at a time, and responsive to a user selection at the ROI selector tool establishing a currently selected CAD finding, modifying the displayed two dimensional image to correspond to at least one image slice in the subset of image slices spanned by the currently selected CAD finding.

12. The method of claim 11, wherein the slice slider bar and the thickness indicator are automatically adjusted to correspond to the image depth and image thickness of the modified two dimensional image responsive to the user selection at the ROI selector tool.

13. The method of claim 11, further comprising visually highlighting the CAD indicator icon for the currently selected CAD finding to make that CAD indicator icon more noticeable relative to the other CAD indicator icons within the outline.

14. The method of claim 1, the slice slider bar extending entirely across the outline.

15. The method of claim 1, the slice slider bar being disposed along the slice ruler at a user-controllable position corresponding to the image depth, the slice slider bar comprising a thickness indicator extending along a distance of the slice ruler corresponding to a thickness of the suspected anatomical abnormality identified by a CAD finding, wherein a current location of the slice slider icon and a size of the thickness indicator are automatically adjusted to correspond to a currently selected CAD finding.

16. The method of claim 1, the image comprising a diagnostic image.

17. A system including at least one processing unit configured to process and display breast x-ray tomosynthesis information according to claim 1.

18. A non-transitory computer readable medium tangibly embodying one or more sequences of instructions wherein execution of the one or more sequences of instructions by one or more processors contained in one or more computing systems causes the one or more computing systems to process and display breast x-ray tomosynthesis information according to claim 1.

* * * * *